US010435562B2

(12) United States Patent
Berlin et al.

(10) Patent No.: US 10,435,562 B2
(45) Date of Patent: Oct. 8, 2019

(54) DERIVATIVES OF NATIVE LIGNIN, LIGNIN-WAX COMPOSITIONS, THEIR PREPARATION, AND USES THEREOF

(71) Applicant: Fibria Innovations Inc., Burnaby (CA)

(72) Inventors: Alex Berlin, Raleigh, NC (US); Paul Mulyk, Vancouver (CA)

(73) Assignee: Fibria Innovations Inc., Vancouver, British Columbia ( * ) Notice: Subject to any disclaimer, the term of this patent is extended or adjusted under 35 U.S.C. 154(b) by 68 days.

(21) Appl. No.: 15/499,585

(22) Filed: Apr. 27, 2017

(65) Prior Publication Data

US 2017/0226344 A1    Aug. 10, 2017

Related U.S. Application Data

(63) Continuation of application No. 13/322,907, filed as application No. PCT/CA2010/000801 on May 27, 2010.

(Continued)

(51) Int. Cl.
*C08L 97/00*        (2006.01)
*D21H 11/00*        (2006.01)
(Continued)

(52) U.S. Cl.
CPC .......... *C08L 97/005* (2013.01); *A23K 10/32* (2016.05); *A23L 33/105* (2016.08); *A61K 36/15* (2013.01); *A61K 36/48* (2013.01); *A61K 36/54* (2013.01); *A61K 36/76* (2013.01); *B27N 3/002* (2013.01); *C07G 1/00* (2013.01); *C08H 6/00* (2013.01); *C08J 3/00* (2013.01); *C08K 5/13* (2013.01); *C08L 23/02* (2013.01); *C08L 57/00* (2013.01); *C08L 91/06* (2013.01); *C08L 97/02* (2013.01); *C09K 15/06* (2013.01); *D21C 11/0007* (2013.01); *D21H 11/00* (2013.01);
(Continued)

(58) Field of Classification Search
CPC ........... C08L 97/005; C07G 1/00; C08H 6/00; C08H 8/00
See application file for complete search history.

(56) References Cited

U.S. PATENT DOCUMENTS 1,358,164 A    11/1920  Kottinger
2,508,735 A *  5/1950   Van Horn ................. C03C 4/00
                                                      501/20

(Continued)

FOREIGN PATENT DOCUMENTS

CA    1136326 A1    11/1982
CA    1201115 A      2/1986
(Continued)

OTHER PUBLICATIONS

English-language machine translation of CN-1421423-A (2003), in ProQuest Dialog, translation done on Nov. 12, 2018. (Year: 2003).*

(Continued)

*Primary Examiner* — Nicholas E Hill
(74) *Attorney, Agent, or Firm* — Perkins Coie LLP; Viola T. Kung

(57) ABSTRACT

A wax composition comprising a lignin derivative wherein the derivative has a total hydroxyl content of from about 0.1 mmol/g to about 7 mmol/g.

17 Claims, 2 Drawing Sheets

Related U.S. Application Data

(60) Provisional application No. 61/233,345, filed on Aug. 12, 2009, provisional application No. 61/182,044, filed on May 28, 2009.

(51) Int. Cl.

| | | |
|---|---|---|
| A61K 36/15 | (2006.01) | |
| A61K 36/48 | (2006.01) | |
| A61K 36/54 | (2006.01) | |
| A61K 36/76 | (2006.01) | |
| C07G 1/00 | (2011.01) | |
| C08H 7/00 | (2011.01) | |
| C08J 3/00 | (2006.01) | |
| C08K 5/13 | (2006.01) | |
| C09K 15/06 | (2006.01) | |
| C08L 23/02 | (2006.01) | |
| C08L 57/00 | (2006.01) | |
| D21C 11/00 | (2006.01) | |
| A23K 10/32 | (2016.01) | |
| A23L 33/105 | (2016.01) | |
| B27N 3/00 | (2006.01) | |
| C08L 91/06 | (2006.01) | |
| C08L 97/02 | (2006.01) | |

(52) U.S. Cl.
CPC ........ C08J 2397/00 (2013.01); C08L 2201/52 (2013.01); C08L 2207/04 (2013.01); Y02P 20/582 (2015.11); Y02P 60/877 (2015.11)

(56) References Cited

U.S. PATENT DOCUMENTS

| | | | |
|---|---|---|---|
| 2,934,531 A | 4/1960 | Gardon et al. | |
| 2,977,352 A | 3/1961 | Gardon et al. | |
| 3,461,082 A | 8/1969 | Otani et al. | |
| 3,546,199 A | 12/1970 | Christian et al. | |
| 3,585,104 A | 6/1971 | Kleinert | |
| 4,100,016 A | 7/1978 | Diebold et al. | |
| 4,279,788 A | 7/1981 | Lambuth | |
| 4,308,033 A * | 12/1981 | Gunnerman | C10L 5/44 44/530 |
| 4,326,036 A | 4/1982 | Hayes | |
| 4,409,032 A | 10/1983 | Paszner et al. | |
| 4,470,851 A | 9/1984 | Paszner et al. | |
| 4,486,557 A | 12/1984 | Gaul et al. | |
| 4,594,130 A | 6/1986 | Chang | |
| 4,612,017 A * | 9/1986 | Lindell | C10L 5/14 44/576 |
| 4,764,596 A | 8/1988 | Lora et al. | |
| 4,918,167 A | 4/1990 | Glasser et al. | |
| 4,964,596 A | 10/1990 | Ganssle et al. | |
| 4,968,771 A | 11/1990 | Baxter | |
| 5,173,527 A | 12/1992 | Calve | |
| 5,196,460 A | 3/1993 | Lora et al. | |
| 5,202,403 A | 4/1993 | Doering | |
| 5,223,601 A | 6/1993 | Chum et al. | |
| 5,344,921 A | 9/1994 | Sudo et al. | |
| 5,373,070 A | 12/1994 | Gardziella et al. | |
| 5,382,608 A | 1/1995 | Gardzielia et al. | |
| 5,411,594 A | 5/1995 | Brelsford | |
| 5,424,417 A | 6/1995 | Torget et al. | |
| 5,681,427 A | 10/1997 | Lora et al. | |
| 5,730,837 A | 3/1998 | Black et al. | |
| 5,756,098 A | 5/1998 | Price et al. | |
| 5,788,812 A | 8/1998 | Agar et al. | |
| 5,879,463 A | 3/1999 | Proenca | |
| 5,911,276 A | 6/1999 | Kieke | |
| 5,916,780 A | 6/1999 | Foody et al. | |
| 6,022,419 A | 2/2000 | Torget et al. | |
| 6,039,276 A | 3/2000 | Hatt et al. | |
| 6,172,204 B1 | 1/2001 | Sarkanen et al. | |
| 6,172,272 B1 | 1/2001 | Shabtai et al. | |
| 6,179,958 B1 | 1/2001 | Lysen et al. | |
| 6,228,177 B1 | 5/2001 | Torget | |
| 6,258,175 B1 | 7/2001 | Lightner | |
| 6,281,328 B1 | 8/2001 | Sartori et al. | |
| 6,342,378 B1 | 1/2002 | Zhang et al. | |
| 6,464,827 B1 | 10/2002 | Colodette | |
| 6,555,350 B2 | 4/2003 | Ahring et al. | |
| 6,632,286 B2 | 10/2003 | Converse | |
| 6,632,931 B1 | 10/2003 | Funaoka | |
| 6,635,695 B2 | 10/2003 | Yoshida et al. | |
| 7,189,306 B2 | 3/2007 | Gervais | |
| 7,413,662 B2 | 8/2008 | Eriksen et al. | |
| 7,413,882 B2 | 8/2008 | Berka et al. | |
| 7,465,791 B1 | 12/2008 | Hallberg et al. | |
| 7,649,086 B2 | 1/2010 | Belanger et al. | |
| 7,842,731 B2 * | 11/2010 | Eckert | B27N 1/006 516/41 |
| 7,947,182 B2 | 5/2011 | Gong | |
| 7,959,765 B2 | 6/2011 | Argyropoulos | |
| 8,067,193 B2 | 11/2011 | Hughes et al. | |
| 8,193,324 B2 | 6/2012 | Hallberg et al. | |
| 8,227,004 B2 | 7/2012 | Hallberg et al. | |
| 8,288,460 B2 | 10/2012 | Balakshin et al. | |
| 8,378,020 B1 | 2/2013 | Balakshin et al. | |
| 8,399,688 B2 | 3/2013 | Dumesic et al. | |
| 8,426,502 B2 | 4/2013 | Balakshin et al. | |
| 8,431,635 B2 | 4/2013 | Balakshin et al. | |
| 8,445,562 B2 | 5/2013 | Balakshin et al. | |
| 9,376,536 B2 | 6/2016 | Berlin | |
| 2002/0069987 A1 | 6/2002 | Pye | |
| 2002/0143085 A1 | 10/2002 | Yoshida et al. | |
| 2003/0070995 A1 | 4/2003 | Breitenbeck | |
| 2005/0234156 A1 * | 10/2005 | Thames | B27N 3/002 524/19 |
| 2006/0264519 A1 | 11/2006 | Eckert et al. | |
| 2007/0034345 A1 | 2/2007 | Petrus et al. | |
| 2007/0141691 A1 | 6/2007 | Hiri | |
| 2007/0172913 A1 | 7/2007 | Hughes et al. | |
| 2007/0259412 A1 | 11/2007 | Belanger | |
| 2008/0021155 A1 | 1/2008 | Bono et al. | |
| 2008/0115415 A1 | 5/2008 | Agrawal et al. | |
| 2008/0262182 A1 | 10/2008 | Funaoka | |
| 2008/0295980 A1 | 12/2008 | Hallberg et al. | |
| 2008/0299629 A1 | 12/2008 | Hallberg et al. | |
| 2008/0317661 A1 | 12/2008 | Eckert et al. | |
| 2009/0062516 A1 | 3/2009 | Belanger et al. | |
| 2009/0062581 A1 | 3/2009 | Appel et al. | |
| 2009/0069550 A1 | 3/2009 | Belanger et al. | |
| 2009/0117226 A1 | 5/2009 | Hallberg et al. | |
| 2009/0118477 A1 | 5/2009 | Hallberg et al. | |
| 2009/0205546 A1 * | 8/2009 | Kluko | C10L 5/363 110/261 |
| 2010/0051558 A1 | 3/2010 | Gong | |
| 2010/0071829 A1 | 3/2010 | Tanzer | |
| 2010/0159517 A1 | 6/2010 | Diner et al. | |
| 2010/0305242 A1 | 12/2010 | Balakshin et al. | |
| 2010/0305243 A1 | 12/2010 | Balakshin et al. | |
| 2010/0305244 A1 | 12/2010 | Balakshin et al. | |
| 2010/0311943 A1 | 12/2010 | Lallave Rivas et al. | |
| 2011/0091711 A1 | 4/2011 | Neivandt et al. | |
| 2011/0236946 A1 | 9/2011 | Maclachlan et al. | |
| 2011/0252701 A1 | 10/2011 | Soane et al. | |
| 2012/0136097 A1 | 5/2012 | Berlin | |
| 2012/0237980 A1 | 9/2012 | Hallberg et al. | |
| 2012/0247617 A1 | 10/2012 | Berlin et al. | |
| 2013/0168323 A1 | 7/2013 | Soane et al. | |
| 2013/0204039 A1 | 8/2013 | Runge | |
| 2013/0228298 A1 | 9/2013 | Balakshin et al. | |
| 2014/0346395 A1 | 11/2014 | Balakshin et al. | |

FOREIGN PATENT DOCUMENTS

| | | | |
|---|---|---|---|
| CA | 1230592 A | 12/1987 | |
| CA | 1278294 C | 12/1990 | |
| CA | 2043399 C | 11/1991 | |
| CA | 2214013 C | 7/1997 | |
| CA | 1339664 C | 2/1998 | |
| CA | 2419658 A1 | 3/2002 | |
| CA | 2611152 A1 | 12/2006 | |

(56) References Cited

FOREIGN PATENT DOCUMENTS

| | | |
|---|---|---|
| CA | 2661202 A1 | 3/2008 |
| CA | 2676982 A1 | 8/2008 |
| CA | 2597135 C | 9/2008 |
| CA | 2687916 A1 | 12/2008 |
| CA | 2696268 A1 | 2/2009 |
| CA | 2697469 A1 | 3/2009 |
| CA | 2743052 A1 | 6/2010 |
| CA | 2715458 A1 | 10/2010 |
| CA | 2798268 C | 8/2011 |
| CA | 2803177 A1 | 1/2012 |
| CN | 1421423 A * | 6/2003 |
| CN | 1766000 A | 5/2006 |
| DE | 199 52 563 A1 | 3/2001 |
| DE | 20 2008 001 703 U1 | 4/2008 |
| EP | 0038677 B1 | 7/1984 |
| EP | 0224721 A1 | 6/1987 |
| EP | 0105937 B1 | 11/1987 |
| EP | 0461463 A2 | 12/1991 |
| EP | 0485150 A1 | 5/1992 |
| EP | 0737253 A1 | 10/1996 |
| GB | 2439135 A | 12/2007 |
| JP | 2007284337 A | 11/2007 |
| JP | 2008005832 A | 1/2008 |
| SE | 527646 C2 | 5/2006 |
| WO | 199315261 A1 | 8/1993 |
| WO | 200075153 A1 | 12/2000 |
| WO | 2007129921 A1 | 11/2007 |
| WO | 2008008793 A1 | 1/2008 |
| WO | 2008137639 A1 | 11/2008 |
| WO | 2008144878 A1 | 12/2008 |
| WO | 2008144903 A1 | 12/2008 |
| WO | 2009003292 A1 | 1/2009 |
| WO | 2009028969 A1 | 3/2009 |
| WO | 2010060183 A1 | 6/2010 |
| WO | 2010081231 A1 | 7/2010 |
| WO | 2010135804 A1 | 12/2010 |
| WO | 2010135805 A1 | 12/2010 |
| WO | 2010135806 A1 | 12/2010 |
| WO | 2010135807 A1 | 12/2010 |
| WO | 2010135832 A1 | 12/2010 |
| WO | 2010135833 A1 | 12/2010 |
| WO | 2011026243 A1 | 3/2011 |
| WO | 2011028554 A1 | 3/2011 |
| WO | 2011097719 A1 | 8/2011 |
| WO | 2011097720 A1 | 8/2011 |
| WO | 2011097721 A1 | 8/2011 |
| WO | 2011106879 A1 | 9/2011 |
| WO | 2011/150504 A1 | 12/2011 |
| WO | 2012000093 A1 | 1/2012 |
| WO | 2012031356 A1 | 3/2012 |
| WO | 2012037668 A1 | 3/2012 |
| WO | 2012126099 A1 | 9/2012 |
| WO | 2012129652 A1 | 10/2012 |
| WO | 2014094104 A1 | 6/2014 |

OTHER PUBLICATIONS

Gosselink, R. J. A., et al. "Analytical protocols for characterisation of sulphur-free lignin." Industrial Crops and Products 19.3 (2004): 271-281. (Year: 2004).*
Tejado, Ayo, et al. "Physico-chemical characterization of lignins from different sources for use in phenol-formaldehyde resin synthesis." Bioresource Technology 98.8 (2007): 1655-1663. (Year: 2007).*
Del Rio, Jose C. et al., "Occurrence of Naturally Acetylated Lignin Units", Journal of Agricultural and Food Chemistry 55.14 (2007): 5461-5468, 2007, pp. 5461-5468.
Luo, Caidian et al., "Identification of potential fermentation inhibitors in conversion of hybrid poplar hydrolyzate to ethanol", Biomass and Bioenergy, 2002, 22, 125-138., Aug. 8, 2001, pp. 125-138.
Mansson, Per, "Quantitative Determination of Phenolic and Total Hydroxyl Groups in Lignins", Holzforschung, 1983, 37, 143-146, 1983, pp. 143-146.
Sun, Xiao-Feng et al., "Extraction and characterization of original lignin and hemicelluloses from wheat straw", J. Agric. Food Chem., 2005, 53, 860-870, Feb. 1, 2005, pp. 860-870.
Tai, D. et al., "Biodegradation of Guaiacyl and Guaiacyl-Syringyl Lignins in Wood by Phanerochaete Chrysosporium", Recent advances in lignin biodeterioration: proceedings of an international seminar, organized under the auspices of the US-Japan cooperative science program. Uni Publishers Co. Ltd. Uni Publishers, 1983., May 31, 1983, pp. 44-63.
Tolbert, Allison et al., "Characterization and Analysis of the Molecular Weight of Lignin for Biorefining Studies", Biofuels, Bioprod. Bioref., 2014, 21 pages, Apr. 14, 2014.
"Baladi Ausadh", Database Traditional Knowledge Digital Library, Database accession No. AJ/697, Narita; Narita Samhita—Translated by Hariharaprasada Tripathi, Chaukhambha Krishnadas Academy (Varanasi), Ed. 1st 2005 pp. 352-353.
"Baloot", DATABASE Traditional Knowledge Digital Library, Database accession No. AN4/83, Ali Ibn-e-Abbaas Majoosi; Kaamil-al-Sena'ah, Part I (10th century Ad), Central Council for Research in Unani Medicine, 61-65 Institutional Area, Janak Puri, New Delhi-58, 2005 AD pp. 190.
"Cincalehah", DATABASE Traditional Knowledge Digital Library, Database accession No. SJ/1103, Rasayoga Sagara—Compiled and Translated by Vaidya Pandita Hariprapanna Ji ,vol. I : Krishnadas Academy, Varanasi, Edn. Reprint, 1999. pp. 442-443.
"Khadiraniryasa Rasa Prayoga", DATABASE Traditional Knowledge Digital Library, Database accession No. RG1/1500, Cakraparlidattah; Cakradattah—Translated by Indradeva Tripathi; Chaukhamba Sanskrit Samsthan (Varanasi), Ed. 4th 2002. pp. 285.
"Majoon-E-Moosli Paak", DATABASE Traditional Knowledge Digital Library, Database accession No. MA3/629, Mohammad Kabiruddin; Bayaaz-e- Kabir, vol. II (Compiled), Daftar-al-Maseeh, Karol Bagh, New Delhi, 1938 AD pp. 173-174.
"Rasayanaristah", DATABASE Traditional Knowledge Digital Library, Database accession No. RS/992, Sodhala; Gadanigrahah ed,Ganga Sahaya Pandeya & Corn.—Indradeva Tripathi,Part-I(Prayoga 2 Khanda) Chaukhamba Sanskrit Sansthan, Varanasi, Ed. 3rd 1999 pp. 392.
"Sanoobar", DATABASE Traditional Knowledge Digital Library, Database accession No. AA21/87E, Abu Bakr Mohammad.Bin Zakariyya Al-Razi; Kitaab-al-Haawi-fil-Tibb, vol.XXI Part I ($9^{th}$ century AD), Dayerah-al-Ma'aarif Usmania, Hyderabad, (First Edition) 1968 AD pp. 128.
"Vasantakusumakararasa", DATABASE Traditional Knowledge Digital Library, Data-base accession No. AK9/717, Cuadmarii; Rasakamadhenu Sarhhita—Edited by Jivaramakalidasa Sastri, Part 4, Chaukhambha Publishers, Varanasi, Edn. 1st 1992 pp. 235.
"Velli Parpam", DATABASE Traditional Knowledge Digital Library, Database accession No. GP01/265, Therayar; Therayar Sekarappa Publisher: C.C.R.A.S, New Delhi.(Edn: 1st, 1979). pp. 200-202.
Akim et al.: 13C NMR of Lignins in Aqueous Alkali, Holzforschung, 51 (1997) 419-427.
Alfani F et al: "Comparison of SHF and SSF processes for the bioconversion of steam-exploded wheat straw", Journal of Industrial Microbiology and Biotechnology, vol. 25, No. 4, Oct. 2000 (Oct. 2000), pp. 184-192, XP002676900.
Arato C. et al. The Lignol approach to biorefining of woody biomass to produce ethanol and chemicals. Applied Biochemistry and Biotechnology—Part A Enzyme Engineering and Biotechnology Mar. 2005 (Mar. 2005), vol. 123 (1-3), pp. 871-882, ISSN: 0273-2289.
Argyropoulos, DS et al. "Isolation of Residual Kraft Lignin in High Yield and Purity" Journal of Pulp and Paper Science 2002, 28, 2, 50-54.
Arlt Jr., HG et al., "Lignin Structure. VIII. Characterization of Ethanol Spruce Lignin Prepared by a New Method"; J. Am. Chem. Soc.; vol. 78, No. 9, pp. 1904-1906 (1956).
Asgari, F et al. "Fundamentals of oxygen delignification. Part II. Functional group for-mation/elimination in residual kraft lignin" Can. J. Chem. 1998, 76, 1606-1615.
Baugh et al. Thermochemical Pretreatment of Lignocellulose to Enhance Methane Fermentation: II. Evaluation and Application of Pretreatment Model, Biotechnology and Bioengineering, vol. 31, pp. 62-70, 1988.

(56) References Cited

OTHER PUBLICATIONS

Brosse, N et al. "Dilute Sulphuric acid and ethanol Organosolv Pretreatment of Miscanthus x Gigan-teus" Celluose Chemistry and Technology 2010, 44, 71-78.

Brosse, N et al. "Pretreatment of Miscanthus x giganteus Using the Ethanol Organolsolv Process for Ethanol Production". hid. Eng. Chem. Res. 2009, 8328-8334.

Cateto et al. "Lignins as Macromonomers for Polyurethane Synthesis: A Comparative Study on Hydroxyl Group Determination", Journal of Applied Polymer Science, vol. 109, 3008-3017 (2008).

Catignani, GL et al. "Antioxidant Properties of Lignin" Journal of Food Science 1982, 1745 and 1748.

Chakar, F.S. et al., "Biobleaching chemistry of laccase-mediator systems on high-lignin-content kraft pulps," Can. J. Chem. 2004, 82, pp. 344-352.

Chakar, FS et al. "Laccase-Lignin Reactions" IPST Technical Paper Series No. 876, Institute of Paper Science and Technology Aug. 2000.

Chandel, et al. "Bioconversion of pentose sugars into ethanol: A review and future directions" Biotechnology and Molecular Biology Review vol. 6(1), pp. 008-020, Jan. 2011.

Colodette et al. "Influence of pulping conditions on eucalyptus kraft pulp yield, quality and bleachability". TAPPI Journal 2002, (1), 14-20.

Crestini et al.: "Structural Analysis of Wheat Straw Lignin by Quantitative 31P and 2D NMR Spectroscopy. The Occurrence of Ester Bonds and a-O-4 Substructures". J. Agric. Food. Chem. 1997, 45, 1212-1219.

Datar, Rohit, et al. "Hydrogen Production from the Fermentation of Corn Stover Biomass Pretreated with a SteamExplosion Process," International Journal of Hydrogen Energy, vol. 32, 13 Nov. 2006, pp. 932-939, XP022094535.

Dizhbite, T. et al., "Characterization of the radical scavenging activity of lignins-natural antioxidants," Bioresource Technology 2004, 95, pp. 309-317.

Dominguez, et al.; "Thermal Stability and Pyrolysis Kinetics of Organosolv Lignins Obtained from Eucalyptus Globulus"; Industrial Crops and Products; vol. 27, No. 2, pp. 150-156 (Dec. 21, 2007).

Dr W.Smith, "Mapping the Development of UK Biorefinery Complexes (NFC07/008)" A Report Prepared for , Tamutech Consultancy, May 2007, 80 pages.

El Hage, R et al. "Characterization of milled wood lignin and ethanol organosolv lignin from miscan-thus". Polymer Degradation and Stability 2009, 94, pp. 1632-1638.

El Hage, R et al. "Effect of the Pre-Treatment Severity on the Antioxidant Properties of Ethanol Organosolv Miscanthus x giganteus Lignin". Natural Resources 2012 (on-line Jun. 2012), 3, 29-34.

El Hage, R et al. "Effects of process severity on the chemical structure of Miscanthus Ethanol organosolv lignin". Polymer Degradation and Stability 2010, 95, 997-1003.

Enoki, A. et al. "Degredation of the Lignin Model Compounds 4-Ethoxy-3METHOXYPHENYLGLYCOL 3-Guaiacyl and Vanillic Acid Ethers by Phanerochaete Chrysosporium", FEMS Microbiology Letters 10, 1981, p. 373.

European Search Report of European Application No. 10779976.9 dated Nov. 14, 2012.

Froass, P.M. et al., "Nuclear Magnetic Resonance Studies. 4. Analysis of Residual Lignin after Kraft Pulping," Ind. Eng. Chem. Res. 1998, 37, pp. 3388-3394.

Gellerstedt. G. et al., "Chemical Structures Present in Biofuel Obtained from Lignin," Energy & Fuels 2008, 22, pp. 4240-4244.

Ghatak et al: "Spectroscopic comparison of lignin separated by electrolysis and acid precipitation of wheat straw soda black liquor", Industrial Crops and Products, Elsevier, NL, vol. 28, No. 2, Sep. 1, 2008 (Sep. 1, 2008), pp. 206-212, XP023178276.

Girisuta B. "Levulinic Acid from Lignocellulosic Biomass", Dissertation Aug. 15, 1975, University of Groningen.

Girisuta B. et al. "A Kinetic Study on the Conversion of Glucose to Levulinic Acid," Icheme Part A 84(A5)339-349, May 2006.

Gosselink et al.: "Analytical protocols for characterization of sulphur-free lignin". Industrial crops and Products 2004, 19, 271-281.

Gosselink, RJA. "Lignin as a reneweable aromatic resource for the chemical industry" Thesis Ibr the degree of doctor at Wageningen University. Dec. 2011, 1-191.

Gregorova, A. et al. "Radical Scavenging Capacity of Lignin and Its Effect on Processing Stabilization of Virgin and Recycled Polypropylene", Journal of Applied Polymer Science, 2007, vol. 106, Issue 3, pp. 1626-1631.

Gregorova, A. et al., "Stabilization effect of lignin in polypropylene and recycled polypropylene," Polymer Degradation and Stability 2005, 89, pp. 553-558.

Hahn-Hagerdal et al., "Ethanolic Fermentation of Pentoses in Lignocellulose Hydrolysates, Applied Biochemistry and Biotechnology", vol. 28/29, 1991, 131-144.

http//\vww.ipst.gatech.edu/faculty_new/faculty_bios/ragauskas/student_presentations/Kosa%20Lignin-SCO.pdf.

Hu, Get al. "Structural Characterization of Switchgrass Lignin atter Ethanol Organosolv Pretreatment". Energy Fuels 2012 (published Dec. 22, 2011) 26, 740-745.

Hussein, et al; "Oil Spill Sorption using Carbonized Pith Bagasse: Trial for Practical Application"; Int. J. Environ. Tech.; vol. 5, No. 2, pp. 233-242 (Mar. 10, 2008).

International Preliminary Report on Patentability dated Nov. 29, 2011 for PCT/CA2010/000801.

International Search Report and Written Opinion dated Aug. 10, 2010 for PCT/CA2010/000801.

Jaaskelainen et al. "The effect of isolation method on the chemical structure of residual lignin". Wood Sci Techno 2003, 37, 91-102.

Jahan, MS et al. "Isolation and Characterization of Lignin from Tropical and Temperate Hardwood" Bangladesh J. Sci. Ind. Res. 2009, 44(3), 271-280.

Jeffries, "Comparison of Alternatives for the Fermentation of Pentoses to Ethanol by Yeasts" In: Lowenstein, M ichael Z., ed. Energy applications of biomass: Proceedings of the National Meeting on Biomass R & D for Energy Applications; Oct. 1-3, 1984; Arlington, VA. New York, NY: Elsevier Applied Science Publishers; 1985 : 231-252.

Kadla, J. F., et al., "Lignin-based carbon fibers for composite fiber applications," Carbon, 2002, 40, 2913-2920.

Kasprzycka-Guttman, T., et al., "Antioxidant properties of lignin and its fractions," Thermochimica Acta 1994, 231, pp. 161-168.

Katzen, R., "Extraction of Lignin from Hydrolyzed Lignocellulose," Ind. Engg. Chem., Dec., 1945, pp. 1218-1222.

Keating Jeffrey D et al: "Tolerance and adaptation of ethanologenic yeasts to lignocellulosic inhibitory compounds", Biotechnology and Bioengineering, vol. 93, No. 6, Apr. 2006 (Apr. 2006), pp. 1196-1206, XP002676901, ISSN: 0006-3592.

Keating, J. D., et al. "An Ethanologenic Yeast Exhibiting Unusual Metabolism in the Fermentation of Lignocellulosic Hexose Sugars", Journal of Industrial Microbiology and Biotechnology, 2004, 31, 235-244.

Kim et al. "Simultaneous consumption of pentose and hexose sugars: an optimal microbial phenotype for efficient fermentation of lignocellulosic biomass" Appl Microbiol Biotechnol (2010) 88:1077-1085.

Kim et al.; "Preliminary Study on Converting Hybrid Poplar to High-Value Chemicals and Lignin Using Organosolv Ethanol Process", Ind. Eng. Chem. Res., Oct. 26, 2010, vol. 49, pp. 12156-12163.

Knutsen, J. and Davis, R.: "Cellulase retention and sugar removal by membrane ul-trafiltration during lignocellulosic biomass hydrolysis", Applied Biochemistry and Biotechnology, 2004, vol. 113-116, pp. 585-599, ISSN: 0273-2289.

Kosa et al. "Characterization of LignoBoost lignin to predict possible utilization". Presentation, Jul. 17, 2009.

Kosikova, B. et al., "Lignin-Stimuiated Protection of Polypropylene Films and DNA in Cells of Mice against Oxidation Damage," BioResources May 2009, 4(2), pp. 805-815.

Kubo, et al.; "Lignin-Based Carbon Fibers: Effect of Synthetic Polymer Blending of Fiber Properties"; Journal of Polymers and the Environment; vol. 13, No. 2, 97-105 (Apr. 1, 2005).

(56) References Cited

OTHER PUBLICATIONS

Kubo, S. et al., "Hydrogen Bonding in Lignin: A Fourier Transform Infrared Model Compound Study," Biomacromolecules 2005, 6, pp. 2815-2821.
Kubo, S. et al., "Kraft Lignin/Poly (ethylene oxide) Blends: Effect of Lignin Structure on Miscibility and Hydrogen Bonding," Journal of Applied Polymer Science 2005, 98, pp. 1437-1444.
Kubo, S. et al., "Poly (Ethylene Oxide)/ Organosolv Lignin Blends: Relationship between Thermal properties, Chemical Structure, and Blend Behaviour"; Macromolecules; vol. 37, pp. 6904-6911 (2004).
Kues, Ursula (Ed.), "Wood Production, Wood Technology and Biotechnological Impacts ", Jan. 1, 2007 (Jan. 1, 2007), Gottingen : Univ.-Verl. Gottingen, 2007, DE, pp. 448.
Kurabi, A., et al. "Enzymatic Hydrolysis of Steam-Exploded and Ethanol Organosolv-Pretreated Douglas-Fir by Novel and Commercial Fungal Cellulases," App. Biochem. Biotech., vol. 121-124, 2005, 219-230.
Liu, H. et al.: "Study on preparation and application in flocculants of modified lignin", Modern Applied Science, Feb. 2011 (Feb. 2011) vol. 5, No. 1, pp. 205-208, 1SSN:1913-1844.
Lucia, LA et al."Comparative Evaluation of Oxygen Delignification Processes for Low- and High-Lignin-Content Softwood Kraft Pulps" Ind. Eng. Chem. Res. 2002, 41, 5171-5180.
Luo; "Lignin-Based Cargon Fiber—Thesis"; University of Maine (May 2010).
Mabee WE et al. "Updates on softwood-to-ethanol process development". Applied Biochemistry and Biotechnology Mar. 2006 (Mar. 2006), vol. 129(1-3), pp. 55-70, ISSN: 0273-2289.
Marchessault, R.H., "Chemrawn Again!," Cellulose, vol. 14, Aug. 2007, pp. 281-282, XP019524885.
Megiatto, J.D. et al., "Sisal Fibers: Surface Chemical Modification Using Reagent Obtained from a Renewable Source; Characterization of Hemicellulose and Lignin as Model Study," J. Agric. Food Chem. 2007, 55, pp. 8576-8584.
Meier et al. On Properties and Degradability of Lignins, Isolated with Alcohol-Water Mixtures. Holzforschung vol. 35 (1981), Part 5, p. 247-252.
Nada A M A et al: "Infrared spectroscopic characteristics of bagasse cresol lignin", Polymer Degradation and Stability, Barking, GB, vol. 43, No. 1, Jan. 1, 1994 (Jan. 1, 1994), pp. 55-59, XP024144586.
Nenkova, et al.; "Study of the Sorption Properties of Technical Hydrolysis Lignin and Wool Shoddy Towards Oil Pollution"; Journal of the University of Chemical Technology and Metallurgy; vol. 43, No. 2, pp. 217-222 (2008).
Nieminen, et al.; "Determination of Hydroxyl Groups in Kraft Pine Lignin by Silicon-29 NMR Spectroscopy"; Holzforschung: International Journal of the Biology, Chemistry, Physics and Technology of Wood; vol. 43, No. 5, pp. 303-307 (Jan. 1, 1989).
Olempska-Beer, Z.: "Alpha-amylase from Bacillus licheniformis containing a genetical-ly engineered alpha-amylase gene from B. licheniformis (thermostable)", 61st JECFA-Chemical and Technical Assessments of Food Additives (CTA), 2004, pp. 1(6)-6(6).
Olson et al.: "Levulinate Esters from Biomass Wastes"; ACS Symposium Series, 2001, vol. 784, Chapter 5, pp. 51-63.
Palmqvist E et al: "Fermentation of Lignocellulosic Hydrolysates I: Inhibition and Detoxification", Bioresource Technology, Elsevier BV, GB, vol. 74, No. 1, Jan. 1, 2000 (Jan. 1, 2000), pp. 17-24, XP001016127.
Pan et al.: "Organosolv Ethanol Lignin from Hybrid Poplar as a Radical Scavenger: Relationship between Lignin Structure, Extraction conditions, and Antioxidant Activity". J. Agric. Food Chem. 2006, 54, 5806-5813.
Pan X. et al. "Biorefining of softwoods using ethanol organosolv pulping: preliminary evaluation of process streams for manufacture of fuel grade ethanol and co-products". Biotechnology and Bioengineering May 20, 2005 (20-4)May 2005), vol. 90(4), pp. 473-481, ISSN: 1097-0290.
Pan, X et al. "The Bioconversion of Mountain Pine Beetle-Killed Lodgepole Pine to Fuel Ethanol Using the Organolsolv Process". Biotechnology and Bioengineering 2008, 101(1). 39-48.
Pan, X.P. et al., "Bioconversion of Hybrid Poplar to Ethanol and Co-Products Using an Organosolv Fractionation Process: Optimization of Process Yields", Biotechnology and Bioengineering, vol. 94, No. 5, pp. 851-861, Aug. 5, 2006 (May 8, 2006), Published online Mar. 7, 2006 (Jul. 3, 2006) in Wiley InterScience (www.interscience.wiley.com).
Pan, X.P. et al., "Pretreatment of Lodgepole Pine Killed by Mountain Pine Beetle Us-ing the Organosolv Process: Fractionation and Process Optimization", Ind. Eng. Chem. Res. 2007, 46, pp. 2609-2617, Published on Web Mar. 14, 2007 (Mar. 14, 2007).
Pasquini D et al: "Extraction of lignin from sugar cane bagasse and Pinus taeda wood chips using ethanol- water mixtures and carbon dioxide at high pressures", Journal of Supercritical Fluids, PRA Press, US, vol. 36, No. 1, Nov. 1, 2005 (Nov. 1, 2005), pp. 31-39, XP027818818, ISSN: 0896-8446.
Pu, Y. et al., "Structural analysis of acetylated hardwood lignins and their photoyellowing properties," Can. J. Chem. 2005, 83, pp. 2132-2139.
Pye, E. Kendall et al. "The Alcell™ process a proven alternative to kraft pulping", Tappi Journal, Mar. 1991, pp. 113-117.
Ruiz-Rosas, et al.; "The Production of Submicron Diameter Carbon Fibers by the Electrospinning of Lignin"; Carbon, Elsevier, Oxford, GB; vol. 48, No. 3, pp. 696-705 (Mar. 1, 2010).
Said, et al.; "Usefulness of Raw Bagasse for Oil Absorption: A Comparison of Raw and Acylated Bagasses and their Components"; Bioresource Technology 100; pp. 2219-2222 (2009).
Sannigrahi, P et al. "Lignin Structural Modifications Resulting from Ethanol Organosolv Treatment of Lob-lolly Pine", Energy Fuels 2010, 24. 683-689.
Sayed, et al.; "Oil Spill Pollution Treatment by Sorption on Natural Cynanchum acutum L. Plant"; Journal of Applied Sciences & Environmental Management; vol. 7, No. 2, pp. 63-73 (Dec. 2003).
Sealey, J et al., "Residual Lignin Studies of Laccase Delignified Kraft Pulps," IPST Technical Paper Series, No. 621, Institute of Paper Science and Technology, Aug. 1996, 7 pages.
Shin-Ichiro, et al.; "Determination of Arylglycerol-beta-aryl Ethers and Other Linkages in Lignins Using DFRC/31P NMR"; Journal of Agricultural and Food Chemistry; vol. 49, No. 2, pp. 536-542 (Feb. 1, 2001).
Shu-Bin Wu et al: "Chemical structures and thermochemical properties of bagasse lignin", Forestry Studies in China, Beijing Forestry University, BE, vol. 8, No. 3, Sep. 1, 2006 (Sep. 1, 2006), pp. 34-37, XP019440259.
Sidiras, D., et al.,"Simulation of acid-catalysed organosolv fractionation of wheat straw," . Bioresource Technology 94 (2004) 98.
Sun, et al.; "Acetylation of Rice Straw with or without Catalysts and its Characterization as a Natural Sorbent in Oil Spill Cleanup"; Journal of Agricultural and Food Chemistry; vol. 50, No. 22, pp. 6428-6433 (Oct. 1, 2002).
Taherzadeh, Mohammad J., et al. "Enzyme-Based Hydrolysis Processes for Ethanol from Lignocellulosic Materials: A Review," Bioresources, vol. 2, Nov. 2007, pp. 707-738, XP008130300.
Tanaka, M. et al.: "Removal of lignin and reuse of cellulases for continuous sacchari-fication of lignocelluloses", Biotechnology and Bioengineering, Sep. 20, 1988 (Sep. 20, 1988) vol. 32, No. 7, pp. 897-902, ISSN: 0006-3592.
Tejado et al.: Physico-chemical characterization of lignins from different sources for use in phenol-formaldehyde resin synthesis. Bioresource Technology 98 (2007) 1655-1663.
Tejado, A et al. "Physico-chemical characterization of lignins from different sources for use in phe-nol-formaldehyde resin synthesis" Bioresource Technology 2007, 98, 1655-1663.
Van Maris, Antonius J A, et al.: "Alcoholic fermentation of carbon sources in biomass hydrolysates by Saccharomyces cerevisiae: current status", Antonie Van Leeuwenhoek, Kluwer Academic Publishers, DO, vol. 90, No. 4, Oct. 11, 2006 (Oct. 11, 2006), pp. 391-418, XP019446684.
Vinardell, M.P. et al., "Potential applications of antioxidant lignins from different sources," Industrial Crops and Products 2008, pp. 220-223.
Vinardell; "Application of Lignins from Different Sources as Antioxidant"; Detergent & Cosmetics; vol. 31, No. 9, pp. 28-30 (Sep. 25, 2008). (English Abstract).

(56) References Cited

OTHER PUBLICATIONS

Wang, Y. et al.: "Application of a novel cationic polyacrylamide as flocculant in treat-ment of papermaking wastewater", Jun. 2010 (Jun. 2010) Bioinformatics and Bio-Medical Engineering, 2010 4th International Conference, pp. 1-4, ISSN: 2151-7614.

Wu et al.: "An Improved Method for Isolating Lignin in High Yield and Purity". Journal of Pulp and Paper Science 2003, 29(7), 235-240.

Wu, et al.; "Development of Lignin/Polyolefin Composites"; China Plastics Industry; vol. 37, No. 6, pp. 1-5 (Jun. 20, 2009). (English Abstract).

Xia et al.: "Quantitative 13C NMR Analysis of Lignins with Internal Standards". J. Agric. Food Chem. 2001, 49, 3573-3378.

Xu et al., Catalytic Liquefaction of Hydrolytic Lignin in Supercritical Ethanol Solution (II): Effect of Reaction Time, Ratio of Solvent/ HL & Atmosphere on Reaction, Acta Energiae Solaris Sinica, 28(7), p. 805-809—English Abstract.

Xu, F., et al., "Comparative study of organosolv lignins from wheat straw," Industrial Crops and Products 23 (2006) 180-193.

Xue, B-L et al. "Polyols Production by Chemical Modification of Autocatalyzed Ethanol-Water lignin from Betula Alnoides". Paper PS-79. Proceedings of the 55th International Convention of Society of IVood Science and Technology Aug. 27-31, 2012, Beijing, China.

Yang, R. et al., "Oxygen Degradation and Spectroscopic Characterization of Hardwood Lignin," Ind. Eng. Chem. Res. 2002, 41, pp. 5941-5948.

Yunqiao, et al.; "Investigation of the Photo-Oxidative Chemistry of Acetylated Softwood Lignin"; Journal of Photochemistry and Photobiology A: Chemistry; vol. 163, No. 1-2, pp. 215-221 (Apr. 15, 2004).

Zawadzki, M. et al., "N-Hydroxy Compounds as New Internal Standards for the 31 P-NMR Determination of Lignin Hydroxy Functional Groups," Holzforschung 2001, 55, 3, pp. 283-285.

Zhang et al. "Removal of Residual Lignin of Ethanol-Based Organosolv Pulp by an Alkalu Extraction Process," J. Applied Polymer Science, 2007, vol. 106, pp. 630.

Zhang, Yi-Heng et al. "Fractionating Recalcitrant Lignocellulose at Modest Reaction Conditions", Biotechnology and Bioengineering, vol. 97, No. 2, Jun. 1, 2007, pp. 214-223.

Zhou Xue-fei "AS-AQ Pulping of Eucalyptus Wood and the Structural Change of Lignin During Pulping". Chemistry and Industry of Forest Products 2004, 24, 107-110 (English Abstract).

Danielle R. Robert et al., "Structural Changes in Lignin During Kraft Cooking Part 3", Journal of Wood Chemistry and Technology, vol. 4, 1984—Issue 3, 1984, p. 239-263.

Pouteau C et al: "Antioxidant properties of lignin in polypropylene", Polymer Degradation and Stabi , Barking, GB, vol. 81, No. 1, Jan. 1, 2003 (Jan. 1, 2003), pp. 9-18, XP004425568, ISSN: 0141-3910, DOI: 10.1016/S0141-3910(03)00057-0.

Boeriu CG et al: "Characterisation of structure-dependent functional properties of lignin with infrared spectroscopy", Industrial Crops and Produ, Elsevier, NL, vol. 20, No. 2, Sep. 1, 2004 (Sep. 1, 2004), pp. 205-218, XP004584665, ISSN: 0926-6690, DOI: 10.1016/J.INDCROP.2004.04.022.

LS Kocheva et al: "Macromolecular Chemistry and Polymeric Materials Structure and Antioxidant Characteristics of Wheat and Oat Lignins", Russian Journal of Applied Chemistry Translated from Zhurnal Prikladnoi Khimii, Jan. 1, 2005 (Jan. 1, 2005), pp. 1343-1350, XP55605357.

\* cited by examiner

DERIVATIVES OF NATIVE LIGNIN, LIGNIN-WAX COMPOSITIONS, THEIR PREPARATION, AND USES THEREOF

This application is a continuation of U.S. application Ser. No. 13/322,907, filed Feb. 27, 2012; which is a national stage of International Application PCT/CA2010/000801, filed May 27, 2010, published Dec. 2, 2010, under PCT Article 21(2) in English; which claims the priority of U.S. Provisional Patent Application Nos. 61/182,044, filed May 28, 2009, and 61/233,345, filed Aug. 12, 2009; the contents of the above applications are incorporated herein by reference in their entirety.

FIELD

This disclosure relates to derivatives of native lignin. This disclosure further relates to wax emulsions comprising derivatives of native lignin such as, for example, those suitable for production of wood composite materials. This disclosure further relates to waxy compositions, processes for their preparation, and methods for their use.

BACKGROUND

Wood composites are among the world's most significant renewable materials. The most common wood composites produced today are oriented strandboard (OSB), plywood, and particle board. Waxes are commonly used in the production of wood composites. The production of wood composites generally includes the blending of dried wood strands and/or particles with a suitable oil-derived liquid wax formulation and an adhesive (resin). These materials are generally derived from non-renewable sources. The wax component may provide water repellant properties that reduce swelling of composites during periods of elevated environmental humidity. The resin components bind wood strands and/or particles to form the composite structures. The addition of wax components to the wood composites is thought to improve the mechanical and physical properties of the panels.

Generally, after blending the wood feedstock with a wax emulsion and a resin, the wood composite is formed by applying suitable pressure at elevated temperatures. Optimal application of pressure and temperature levels are determined from the specifications of the wax and resin components used, the type of composite being produced, and the tree species from which the wood fibers and/or strands and/or particles are produced. Once the wood composites are produced, a number of quality/performance characteristics are determined including, thickness swell, water adsorption, modulus of rupture, modulus of elasticity, internal bond, among others. The testing protocols for each type of wood composite have been well-defined by the respective regulatory bodies. Examples of these standards include: the Canadian Standards Association (CSA) O112.6-M1977 Phenol and Phenol-Resorcinol Resin Adhesives for Wood (High-Temperature Curing), the CSA O437.1-93 Test Methods for OSB and Waferboard, or the CSA Standard O151-04 Canadian softwood plywood. Before the commercialization of new resin (adhesive) it is usually necessary for them to meet the established standards such as the ones listed above.

Native lignin is a naturally occurring amorphous complex cross-linked organic macro-molecule that comprises an integral component of all plant biomass. Extracting native lignin from lignocellulosic biomass during pulping generally results in lignin fragmentation into numerous mixtures of irregular components. Furthermore, the lignin fragments may react with any chemicals employed in the pulping process. Consequently, the generated lignin fractions can be referred to as lignin derivatives and/or technical lignins. As it is difficult to elucidate and characterize such complex mixture of molecules, lignin derivatives are usually described in terms of the lignocellulosic plant material used, and the methods by which they are generated and recovered from lignocellulosic plant material, i.e. hardwood lignins, softwood lignins, and annual fibre lignins.

Given that lignin derivatives are available from renewable biomass sources there is an interest in using these derivatives in certain industrial applications. For example, lignin derivatives obtained via organosolv extraction, such as the Alcell® process (Alcell is a registered trademark of Lignol Innovations Ltd., Burnaby, BC, CA), have been used in rubber products, adhesives, resins, plastics, asphalt, cement, casting resins, agricultural products, oil-field products and as feedstocks for the production of fine chemicals. It has been suggested to use lignin-modified phenol-formaldehyde resin as an adhesive for wood composites (see, for example, U.S. Pat. No. 5,010,156; WO93/21260; WO94/24192).

However, large-scale commercial application of the extracted lignin derivatives, has been limited due to, for example, the inconsistency of their chemical and functional properties. This inconsistency may, for example, be due to changes in feedstock supplies and the particular extraction/generation/recovery conditions. These issues are further complicated by the complexity of the molecular structures of lignin derivatives produced by the various extraction methods and the difficulty in performing reliable routine analyses of the structural conformity and integrity of recovered lignin derivatives.

Despite the advantages of lignin, for a variety of reasons, it has not been adopted for widespread use in wood composites. For instance, it is often problematic to provide lignins that have acceptable and consistent performance characteristics. Additionally, the cost of producing and/or purifying the lignin may make it uneconomic for certain uses. Furthermore, incorporation of high levels of lignin in phenol-formaldehyde resin can lead to undesirably high end-point viscosities.

SUMMARY

The present disclosure provides derivatives of native lignin having a certain hydroxyl content. Surprisingly, it has been found that consistent and predictable properties may be provided by selecting for derivatives of native lignin having certain hydroxyl contents.

The present disclosure provides derivatives of native lignin having a total hydroxyl content of from about 0.1 mmol/g to about 7 mmol/g. Such lignins have surprisingly been found to have an appropriate hydrophobicity for use in the wax component in the production of wood composites.

As used herein, the term "native lignin" refers to lignin in its natural state, in plant material.

As used herein, the terms "lignin derivatives" and "derivatives of native lignin" refer to lignin material extracted from lignocellulosic biomass. Usually, such material will be a mixture of chemical compounds that are generated during the extraction process.

Some exemplary embodiments of the present disclosure relate to lignin-modified wax composition, such as an emulsion or a suspension, suitable for production of composite materials exemplified by composite wood products and the like.

Some exemplary embodiments of the present disclosure relate to lignin derivatives suitable for production of lignin-modified wax compositions. Suitable lignin derivatives generally comprise lignin derivatives that are solubilized from lignocellulosic biomass by an organosolv process.

This summary does not necessarily describe all features of the invention. Other aspects, features and advantages of the invention will be apparent to those of ordinary skill in the art upon review of the following description of specific embodiments of the invention.

BRIEF DESCRIPTION OF THE DRAWINGS

The present disclosure will be described in conjunction with reference to the following drawings, in which.

DETAILED DESCRIPTION

Figure 1:
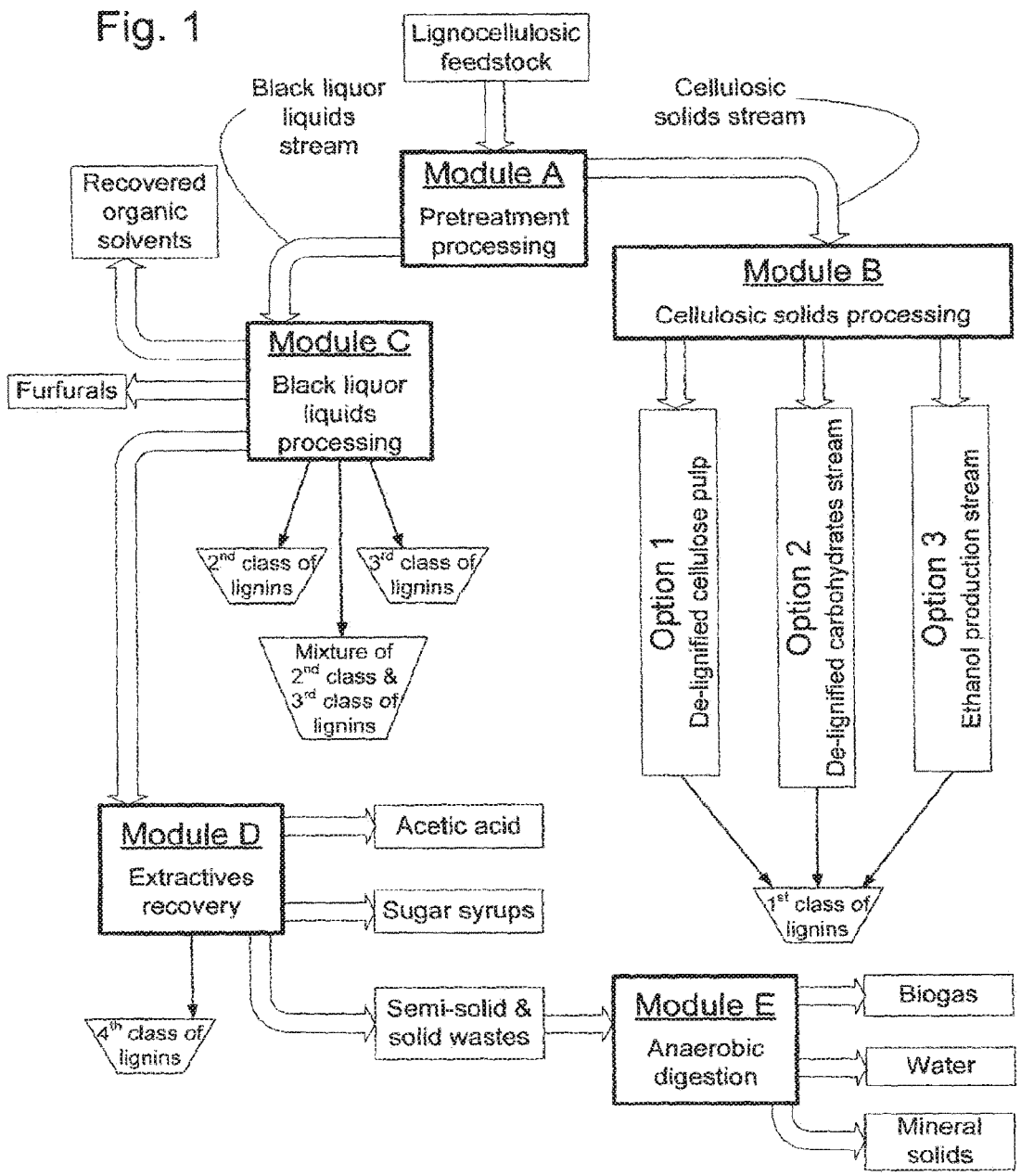
FIG. 1 is a schematic flowchart showing various exemplary embodiments of a modular biorefinery processing system for recovery of four distinct structural classes of lignin derivatives from lignocellulosic feedstocks with organic solvents.
Figure 2:
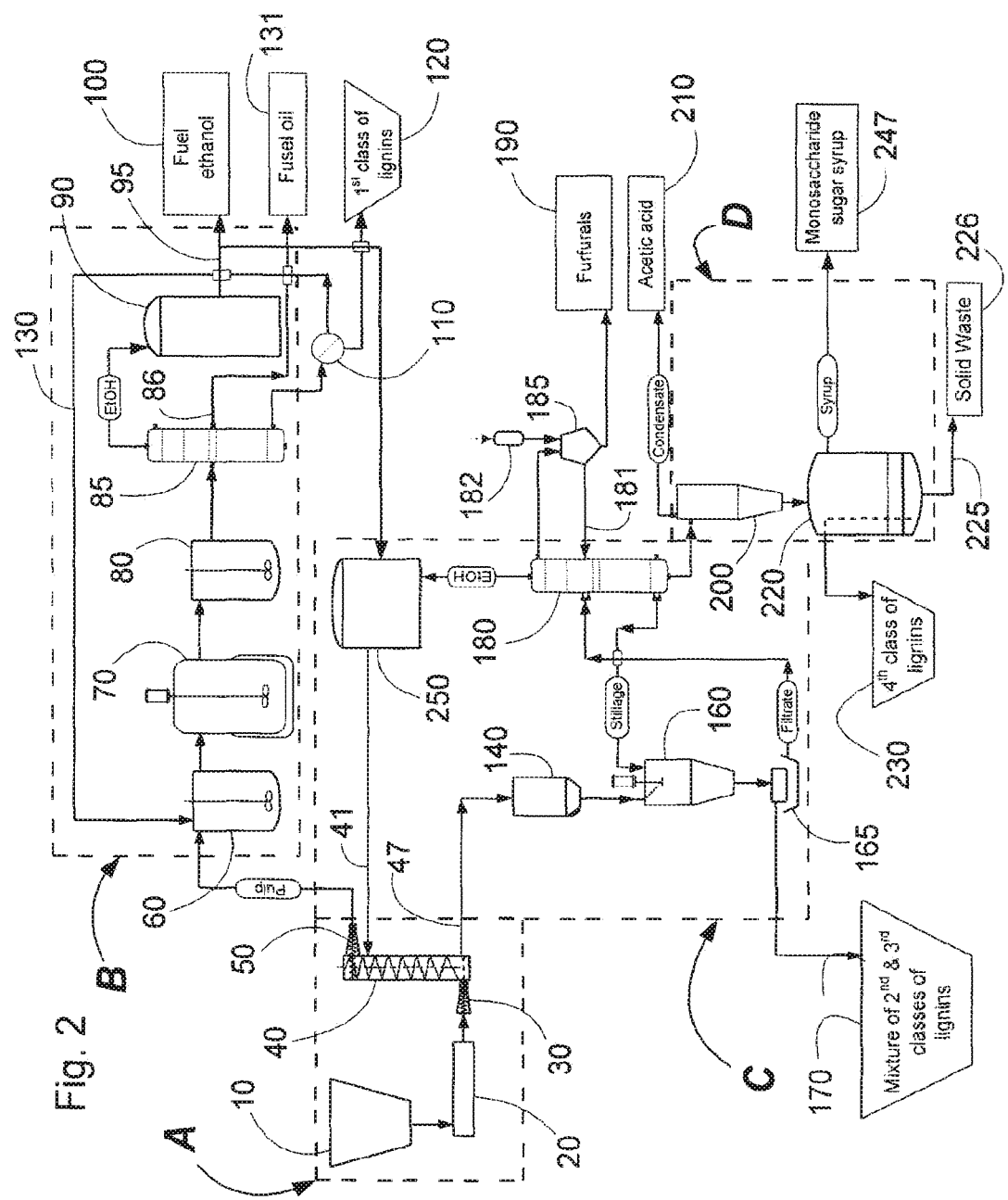
FIG. 2 is a schematic flowchart of an exemplary modular continuous counter-flow biorefinery system configured for separation and recovery of three lignin solids fractions from a lignocellulosic feedstock.

The present disclosure provides derivatives of native lignin having a total hydroxyl content of from about 0.1 mmol/g to about 7 mmol/g. The present lignin derivatives may have a total hydroxyl content of from about 1 mmol/g, about 2 mmol/g, 3.5 mmol/g, 4 mmol/g, 4.5 mmol/g, or greater. The present lignin derivatives may have a total hydroxyl content of from about 6.8 mmol/g, about 6.7 mmol/g, about 6.6 mmol/g, about 6.5 mmol/g, or less.

The present lignin derivatives may be used in the production of wood composite materials. Examples of wood composites include low density fibreboard (LDF), medium density fibreboard (MDF), high density fibreboard (HDF), strawboard & other agricultural fibre/particle boards, oriented strand board (OSB), particle board, plywood, and the like. The present lignin derivatives may be used in the production of wood-plastic composites.

The present lignin derivatives may be incorporated into the wax compositions useful in the manufacture of wood composites. The present wax composition may be an emulsion, suspension, or the like.

The present wax compositions preferably comprise, on the basis of the solid contents, about 50% or less, about 45% or less, about 40% or less, about 35% or less, about 30% or less, of lignin derivative. The present wax compositions preferably comprise, on the basis of the solid contents, about 0.1 or greater, about 1% or greater, about 5% or greater, about 10% or greater, about 15% or greater, about 20% or greater, of lignin derivative.

Presently, it is common to use "slack waxes" in the manufacture of wood composites. Slack was is a by-product of the oil refining process and, as such, is a non-renewable resource whose cost is subject to the vagaries of crude oil prices. Furthermore, changes in oil-refinery practices, such as catalytic dewaxing, are eliminating slack-wax as a by-product.

The present wax compositions may comprises a variety of waxes including, but not limited to, fossil waxes (e.g. montan, ozocerite, pyropissite, and the like); non-fossil waxes such as animal or vegetable waxes (e.g. bees wax, plant waxes such as carnauba or candelilla, and the like); partially synthetic waxes (e.g. alcohol waxes, wool wax, and the like); synthetic waxes (e.g. amide waxes, polyethylene waxes, Fischer-Tropsch, polyolefins, Ziegler process wax, and the like); petroleum waxes such as macro-crystalline waxes or microcrystalline waxes (e.g. paraffins, slack wax, slack wax raffinates, decoiled slack wax, soft wax, semi-refined wax, filtered wax, fully refined wax, bright stock wax, plastic microwaxes, hard microwaxes, and the like); and combinations thereof. Preferred waxes for use herein include, petroleum waxes, synthetic waxes, and combinations thereof. For example, the present wax may be a slack wax.

The present compositions preferably comprise, on the basis of the solid contents, about 90% or less, about 80% or less, about 70% or less, of wax. The present compositions preferably comprise, on the basis of the solid contents, about 20% or greater, about 30% or greater, about 40% or greater, about 50% or greater, of wax.

The present compositions may comprise a variety of optional components such as, for example, water, stabilizer, emulsifier, and combinations thereof.

Exemplary embodiments of the present disclosure relate to lignin-modified wax emulsions suitable for production of wood composite materials such as, but not limited to, oriented strandboard (OSB), plywood, and laminated veneerlumber (LVL). For example, the present lignin derivatives may be commingled with commercial slack wax compositions to produce lignin-modified slack wax emulsions. Certain exemplary lignin-modified wax emulsions may be prepared by intermixing a wax or its components with a surface tension/interfacial tension reducing agent such as lignosulphonates, isogenic lignin derivatives, ionogenic detergents (e.g. sodium dodecyl sulfate and the like), lignin solubilizing agents (e.g. sodium hydroxide, potassium hydroxide, concentrated soda solutions), strong nitrogen bases, and the like; and the present lignin derivatives. Such exemplary emulsions may comprise at least 20% replacement of solids with the lignin derivatives. The lignin-modified wax emulsions are preferably stable and provide bonding and stability performance that is similar to commercial wax emulsions when applied to wood composites. The levels of lignin derivatives that may be incorporated into such modified wax emulsions can be further increased by hydrophobization of the lignin derivatives by chemical modification or by modified biomass processing conditions. Such lignin-modified wax emulsions may be suitable replacements for oil-derived slack wax compositions that are commonly used for commercial production of wood composite materials.

The present invention provides derivatives of native lignin recovered during or after pulping of lignocellulosic feedstocks. The pulp may be from any suitable lignocellulosic feedstock including hardwoods, softwoods, annual fibres, and combinations thereof.

Hardwood feedstocks include *Acacia; Afzelia; Synsepalum duloificum; Albizia;* Alder (e.g. *Alnus glutinosa, Alnus rubra*); Applewood; *Arbutus;* Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophylla*); Beech (e.g. *F. glvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubinga; Buckeye (e.g. *Aesculus hippocastanum,*

*Aesculus glabra, Aesculus flava/Aesculus octandra*); Butternut; Catalpa; Cherry (e.g. *Prunus serotina, Prunus pennylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ipê; Iroko; Ironwood (e.g. Bangkirai, *Carpinus caroliniana, Casuarina equisetifolia, Choricbangarpia subargentea, Copaifera* spp., *Eusideroxylon zwageri, Guajacum officinale, Guajacum sanctum, Hopea odorata,* Ipe, *Krugiodendron ferreum, Lyonothamnus lyonii* (*L. floribundus*), *Mesua ferrea, Olea* spp., *Olneya tesota, Ostrya virginiana, Parrotia persica, Tabebuia serratifolia*); Jacaranda; Jotoba; Lacewood; Laurel; Limba; Lignum vitae; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoumé; Oregon Myrtle; California Bay Laurel; Pear; Poplar (e.g. *P. balsamifera, P. nigra,* Hybrid Poplar (*Populus×canadensis*)); Ramin; Red cedar; Rosewood; Sal; Sandalwood; Sassafras; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations/hybrids thereof.

Softwood feedstocks include *Araucania* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arionica, Taxodium distichum, Chamaecyparis obtusa, Chamaegparis lawsoniana, Cupressus semperviren*); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Annual fibre feedstocks include biomass derived from annual plants, plants which complete their growth in one growing season and therefore must be planted yearly. Examples of annual fibres include: flax, cereal straw (wheat, barley, oats), sugarcane bagasse, rice straw, corn stover, corn cobs, hemp, fruit pulp, alfa grass, switchgrass, and combinations/hybrids thereof. Industrial residues like corn cobs, fruit peals, seeds, etc. may also be considered annual fibres since they are commonly derived from annual fibre biomass such as edible crops and fruits. For example, the annual fibre feedstock may be selected from wheat straw, corn stover, corn cobs, sugar cane bagasse, and combinations/hybrids thereof.

The derivatives of native lignin will vary with the type of process used to separate native lignins from cellulose and other biomass constituents. Preparations very similar to native lignin can be obtained by (1) solvent extraction of finely ground wood (milled-wood lignin, MWL) or by (2) acidic dioxane extraction (acidolysis) of wood. Derivatives of native lignin can be also isolated from biomass pretreated using (3) steam explosion, (4) dilute acid hydrolysis, (5) ammonia fibre expansion, (6) autohydrolysis methods. Derivatives of native lignin can be recovered after pulping of lignocellulosics including industrially operated kraft, soda pulping (and their modifications) or sulphite pulping. In addition, a number of various pulping methods have been developed but not industrially introduced. Among them four major "organosolv" pulping methods tend to produce highly-purified lignin mixtures. The first organosolv method uses ethanol/solvent pulping (aka the Alcell® process); the second organosolv method uses alkaline sulphite anthraquinone methanol pulping (aka the "ASAM" process); the third organosolv process uses methanol pulping followed by methanol, NaOH, and anthraquinone pulping (aka the "Organocell" process); the fourth organosolv process uses acetic acid/hydrochloric acid or formic acid pulping (aka the "Acetosolv" process).

It should be noted that kraft pulping, sulphite pulping, and ASAM organosolv pulping will generate derivatives of native lignin containing significant amounts of organically-bound sulphur which may make them unsuitable for certain uses. Acid hydrolysis, soda pulping, steam explosion, Alcell® pulping, Organocell pulping, and Acetosolv pulping will generate derivatives of native lignin that are sulphur-free or contain low amounts of inorganic sulphur.

Organosolv processes, particularly the Alcell® process, tend to be less aggressive and can be used to separate highly purified lignin derivatives and other useful materials from biomass without excessively altering or damaging the native lignin building blocks. Such processes can therefore be used to maximize the value from all the components making up the biomass. Organosolv extraction processes however typically involve extraction at higher temperatures and pressures with a flammable solvent compared to other industrial processes and thus are generally considered to be more complex and expensive.

A description of the Alcell® process can be found in U.S. Pat. No. 4,764,596 (herein incorporated by reference). The process generally comprises pulping or pre-treating a fibrous biomass feedstock with primarily an ethanol/water solvent solution under conditions that include: (a) 60% ethanol/40% water, (b) temperature of about 180° C. to about 210° C., (c) pressure of about 20 atm to about 35 atm, and (d) a processing time of 5-120 minutes. Derivatives of native lignin are fractionated from the native lignins into the pulping liquor which also receives solubilised hemicelluloses, other carbohydrates and other extractives such as resins, organic acids, phenols, and tannins. Organosolv pulping liquors comprising the fractionated derivatives of native lignin and other extractives from the fibrous biomass feedstocks, are often called "black liquors". The organic acid and extractives released by organosolv pulping significantly acidify the black liquors to pH levels of about 5 and lower. After separation from the cellulosic pulps produced during the pulping process, the derivatives of native lignin are recovered from the black liquors by depressurization followed by flashing with cold water which will cause the fractionated derivatives of native lignin to precipitate thereby enabling their recovery by standard solids/liquids separation processes. Various disclosures exemplified by U.S. Pat. No. 7,465,791 and PCT Patent Application Publication No. WO 2007/129921, describe modifications to the Alcell organosolv process for the purposes of increasing the yields of fractionated derivatives of native lignin recovered from fibrous biomass feedstocks during biorefining. Modifications to the Alcell organosolv process conditions included adjusting: (a) ethanol concentration in the pulping liquor to a value selected from a range of 35%-85% (w/w) ethanol, (b) temperature to a value selected from a range of 100° C. to 350° C., (c) pressure to a value selected from a range of 5 atm to 35 atm, and (d) processing time to a duration from a range of 20 minutes to about 2 hours or longer, (e) liquor-to-wood ratio of 3:1 to 15:1 or higher, (f) pH of the cooking liquor from a range of 1 to 6.5 or higher if a basic catalyst is used.

The present invention provides a process for producing derivatives of native lignin, said process comprising:

(a) pulping a fibrous biomass feedstock with an organic solvent/water solution, (b) separating the cellulosic pulps or pre-treated substrates from the pulping liquor or pre-treatment solution, (c) recovering derivatives of native lignin.

The organic solvent may be selected from short chain primary and secondary alcohols, such as such as methanol, ethanol, propanol, and combinations thereof. For example, the solvent may be ethanol. The liquor solution may comprise about 20%, by weight, or greater, about 30% or greater, about 50% or greater, about 60% or greater, about 70% or greater, of ethanol.

Step (a) of the process may be carried out at a temperature of from about 100° C. and greater, or about 120° C. and greater, or about 140° C. and greater, or about 160° C. and greater, or about 170° C. and greater, or about 180° C. and greater. The process may be carried out at a temperature of from about 300° C. and less, or about 280° C. and less, or about 260° C. and less, or about 240° C. and less, or about 220° C. and less, or about 210° C. and less, or about 205° C. and less, or about 200° C. and less.

Step (a) of the process may be carried out at a pressure of about 5 atm and greater, or about 10 atm and greater, or about 15 atm and greater, or about 20 atm and greater, or about 25 atm and greater, or about 30 atm and greater. The process may be carried out at a pressure of about 150 atm and less, or about 125 atm and less, or about 115 atm and less, or about 100 atm and less, or about 90 atm and less, or about 80 atm and less.

The fibrous biomass may be treated with the solvent solution of step (a) for about 1 minute or more, about 5 minutes or more, about 10 minutes or more, about 15 minutes or more, about 30 minutes or more. The fibrous biomass may be treated with the solvent solution of step (a) at its operating temperature for about 360 minutes or less, about 300 minutes or less, about 240 minutes or less, about 180 minutes or less, about 120 minutes or less.

The pH of the pulp liquor may, for example, be from about 1 to about 6, or from about 1.5 to about 5.5.

The weight ratio of liquor to biomass may be any suitable ratio. For example, from about 5:1 to about 15:1, from about 5.5:1 to about 10:1; from about 6:1 to about 8:1.

The volume of extraction solution is from about 5 to about 10 times the volume of the biomass feedstock. For example, the volume of extraction solution may be from about 6 to about 8 times that of the biomass The present disclosure provides a process for producing a lignin derivative having a total hydroxyl content of about 0.1 mmol/g to about 7 mmol/g. Said process comprises:

a) pulping or pre-treating a fibrous biomass feedstock in a vessel with an organic solvent/water solution to form a liquor, wherein:
 i. the solution comprises about 30% or greater, by weight, of organic solvent; and
 ii. the pH of the liquor is from about 1 to about 6;

b) heating the liquor to about 100° C. or greater;

c) raising the pressure in the vessel to about 5 atm or greater;

d) maintaining the elevated temperature and pressure for 1 minute or longer;

e) separating the cellulosic pulps from the pulp liquor

The present lignin derivatives may comprise alkoxy groups. For example, the present lignin derivatives may have an alkoxy content of 2 mmol/g or less; about 1.4 mmol/g or less; about 1.2 mmol/g or less; about 1 mmol/g or less; about 0.8 mmol/g or less; about 0.7 mmol/g or less; about 0.6 mmol/g or less; about 0.5 mmol/g or less; about 0.4 mmol/g or less; about 0.3 mmol/g or less. The present lignin derivatives may have an alkoxy content of 0.001 mmol/g or greater, about 0.01 mmol/g of greater, about 0.05 mmol/g or greater, about 0.1 mmol/g or greater.

The present lignin derivatives may comprise ethoxyl groups. For example, the present lignin derivatives may have an ethoxyl content of 2 mmol/g or less; about 1.4 mmol/g or less; about 1.2 mmol/g or less; about 1 mmol/g or less; about 0.8 mmol/g or less; about 0.7 mmol/g or less; about 0.6 mmol/g or less; about 0.5 mmol/g or less; about 0.4 mmol/g or less; about 0.3 mmol/g or less. The present lignin derivatives may have an ethoxyl content of 0.001 mmol/g or greater, about 0.01 mmol/g of greater, about 0.05 mmol/g or greater, about 0.1 mmol/g or greater.

The present lignin derivatives may have any suitable phenolic hydroxyl content such as from about 2 mmol/g to about 8 mmol/g. For example, the phenolic hydroxyl content may be from about 2.5 mmol/g to about 7 mmol/g; about 3 mmol/g to about 6 mmol/g.

The present lignin derivatives may have any suitable number average molecular weight (Mn). For example, the Mn may be from about 200 g/mol to about 3000 g/mol; about 350 g/mol to about 2000 g/mol; about 500 g/mol to about 1500 g/mol.

The present lignin derivatives may have any suitable weight average molecular weight (Mw). For example, the Mw may be from about 500 g/mol to about 5000 g/mol; about 750 g/mol to about 4000 g/mol; about 900 g/mol to about 3500 g/mol.

The present lignin derivatives may have any suitable polydispersity (Ð). For example, the Ð may be from about 1 to about 5; from about 1.2 to about 4; from about 1.3 to about 3.5; from about 1.4 to about 3.

The present lignin derivatives are preferably hydrophobic. Hydrophobicity may be assessed using standard contact angle measurements. In the case of lignin a pellet may be formed using a FTIR KBr pellet press. Then a water droplet is added onto the pellet surface and the contact angle between the water droplet and the lignin pellet is measured using a contact angle goniometer. As the hydrophobicity of lignins increases the contact angle also increases. Preferably the lignins herein will have a contact angle of about 90° or greater. In the case of the use of lignin in wax emulsions the lignins are preferably very hydrophobic so as to resemble paraffin and provide maximum water repellent properties.

As used herein the term "total hydroxyl content" refers to the quantity of hydroxyl groups in the lignin derivatives and is the arithmetic sum of the quantity of aliphatic and phenolic hydroxyl groups (OHtot=OHal+OHph). OHal is the arithmetic sum of the quantity of primary and secondary hydroxyl groups (OHal=OHpr+OHsec). The hydroxyl content can be measured by quantitative $^{13}C$ high resolution NMR spectroscopy of acetylated and non-acetylated lignin derivatives, using, for instance, 1,3,5-trioxane and tetramethyl silane (TMS) as internal reference. For the data analysis "BASEOPT" (DIGMOD set to baseopt) routine in the software package TopSpin 2.1.4 was used to predict the first FID data point back at the mid-point of $^{13}C$ r.f. pulse in the digitally filtered data was used. For the NMR spectra recording a Bruker AVANCE II digital NMR spectrometer running TopSpin 2.1 was used. The spectrometer used a Bruker 54 mm bore Ultrashield magnet operating at 14.1 Tesla (600.13 MHz for $^1H$, 150.90 MHz for $^{13}C$). The spectrometer was coupled with a Bruker QNP cryoprobe (5 mm NMR samples, $^{13}C$ direct observe on inner coil, $^1H$ outer coil) that had both coils cooled by helium gas to 20K and all preamplifiers cooled to 77K for maximum sensitivity. Sample temperature was maintained at 300 K±0.1 K using a Bruker BVT 3000 temperature unit and a Bruker BCU05 cooler with ca. 95% nitrogen gas flowing over the sample tube at a rate of 800 L/h.

Quantification of ethoxyl groups was performed similarly to aliphatic hydroxyls quantification by high resolution $^{13}C$ NMR spectroscopy. Identification of ethoxyl groups was confirmed by 2D NMR HSQC spectroscopy. 2D NMR spectra were recorded by a Bruker 700 MHz UltraShield Plus standard bore magnet spectrometer equipped with a sensitive cryogenically cooled 5 mm TCI gradient probe with inverse geometry. The acquisition parameters were as follow: standard Bruker pulse program hsqcetgp, temperature of 298 K, a 90° pulse, 1.1 sec pulse delay (d1), and acquisition time of 60 msec.

The present disclosure provides a method of producing a composite wood product, said method comprising:
  a. Obtaining a cellulosic fibre material;
  b. Obtaining an adhesive suitable for adhering the fibres of said material;
  c. Mixing said cellulosic material with said adhesive, forming the mixture into a suitable shape and curing; and
  d. Applying a wax composition according to the present disclosure to the shaped article.

While the present wax compositions are useful in the production of composite wood products, they also have other utilities. For example, the present wax compositions may be used in paints/lacquers, printing inks, textiles, floor polishes/protectants, façade protection, wood/timber protection, mold release, tube drawing, agricultural uses, automotive polishes, packaging films, temporary protective coatings, food coatings, metal working, alkali strippable coatings, anti-transpiration, paper & board (coatings/lubricants, sixing, corrugated board treatment, transfer papers, wet-strength improvement, printability improvement), glass lubrication, glass fibre sizing, insecticide stickers, leather treatment, and the like.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

The following examples are intended to be exemplary of the invention and are not intended to be limiting.

EXAMPLES

Example 1: Preparation of Lignin-Modified Wax Emulsions Using Sodium Hydroxide as a Solubilizing Agent at Medium Slack Wax Replacement Levels An exemplary lignin-modified slack wax emulsion was prepared with the follow process:
(a) a selected amount of a Reax® 85A (Reax is a registered trademark of the MeadWestvaco Corporation, Glen Allen, Va., USA), a commercial lignosulphonate (LS) was dissolved in suitable volume of water;
(b) a selected amount of sodium hydroxide (NaOH) was mixed into the solution;
(c) a selected amount of a mixture of lignin derivatives was mixed into the solution;
(d) the solution was filtered to produce a filtrate; and
(e) the filtrate then was then mixed into a selected volume of a commercial slack wax emulsion (EW-58S, Hexion Specialty Chemicals, Columbus, Ohio, USA) to produce a stable lignin-modified wax emulsion. The EW-58S wax emulsion contained 58% solids. The lignin derivatives were produced by organosolv pulping of a batch of aspen chips. The black liquor generated during the organosolv pulping was separated from the pulp solids materials, and then was rapidly diluted with cold water which caused precipitation of lignin derivatives. The lignin derivatives were separated from the de-lignified liquor and dried prior to use. The processing conditions and physico-chemical properties of the lignin derivatives recovered after organosolv pulping of the aspen wood chips, are shown in Table 1.

TABLE 1

| Biomass processing parameter | |
| --- | --- |
| Acid (% odw feed) | 0 |
| Cooking time (min) | 60 |
| Cooking temperature (° C.) | 193 |
| Ethanol concentration in cooking liquor (% wt.) | 50 |
| Lignin derivatives yield (% total native lignin) | 60 |
| Characteristics of lignin derivatives | |
| Primary hydroxyl groups (mmol/g) | 0.95 |
| Secondary hydroxyl groups (mmol/g) | 0.79 |

TABLE 1-continued

| | |
| --- | --- |
| Aliphatic hydroxyl groups (mmol/g) | 1.74 |
| Phenolic hydroxyl groups (mmol/g) | 4.21 |
| Total hydroxyl groups (mmol/g) | 5.95 |
| Methoxyl groups (mmol/g) | 6.32 |
| Ethoxyl groups (mmol/g) | 0.68 |
| Syringyl groups (mmol/g) | 4.84 |
| Guaiacyl groups (mmol/g) | 1.89 |
| Degree of condensation (DC) | 33 |
| Number-average molecular weight (Mn, g/mol) | 887 |
| Weight-average molecular weight (Mw, g/mol) | 1,808 |
| Z average molecular weight (Mz, g/mol) | 3,650 |
| Polydispersity (D) | 2.04 |
| Glass transition point (Tg, ° C.) | 61 |
| Thermal Flow Index at 105° C. (mm) | 24 |
| Thermal Flow Index at 120° C. (mm) | 37 |
| Thermal Flow Index at 150° C. (mm) | 69 |
| Thermal Flow Index at 180° C. (mm) | 82 |
| Melt Flow Index (g lignin derivatives/10 min measured at 160° C.) | ~50 |
| Normalized specific Internal bond strength at 120° C. (MPa/cm$^2$/mg) | 2.9 |
| Normalized specific Internal bond strength at 150° C. (MPa/cm$^2$/mg)* | 3.6 |
| Normalized specific Internal bond strength at 180° C. (MPa/cm$^2$/mg)* | 4.9 |

*Measured at 30% replacement level by a lignin derivative of a commercial OSB phenolic resin.

Favourable emulsifying conditions for incorporation of the lignin derivatives into a slack wax emulsion were achieved. Several lignin-modified wax emulsion formulations were prepared by combining solutions produced by following steps (a)-(d) that incorporated mixtures of lignin derivatives recovered from different types of hardwood lignocellulosic feedstocks, with the EW-58S wax emulsion. Several other lignin-modified wax emulsions were prepared by proportionally increasing the amounts of mixtures of lignin derivatives incorporated into the EW-58S wax emulsions. The LS was added to all samples, as a surface tension/interfacial tension reducing agent, in a fixed amount to yield a final concentration of 0.03%. A range of solutions with varying concentrations of NaOH were prepared while mixtures of lignin derivatives were added in excess (Table 2). Excess lignin derivatives were filtered out. The remaining supernatants containing the lignin derivatives were intermixed into the EW-58S wax emulsions in a 1:1 volume ratio. The solutions were mixed thoroughly and then left to stand for 24 hrs.

Modified-lignin wax emulsion samples 1-4 (Table 2) formed a solid black mass when intermixed into the commercial slack wax emulsion and produced a non-liquid formulation with limited suitability for wood composites applications.

TABLE 2

| Sample ID | 7.4% NaOH added (mL) | Water (mL) | LS (mL) | Lignin derivatives (g) | Final NaOH (%) | Final LS (%) | Final NaOH (%) | Comments |
| --- | --- | --- | --- | --- | --- | --- | --- | --- |
| 1 | 12 | 0 | 0 | 1.0211 | 5.00 | 0 | 5.00 | Solid broken |
| 2 | 10 | 0 | 2 | 1.0519 | 4.17 | 0.03 | 4.17 | Solid broken |
| 3 | 5 | 5 | 2 | 1.0508 | 2.08 | 0.03 | 2.08 | Solid broken |
| 4 | 2.5 | 7.5 | 2 | 0.9732 | 1.04 | 0.03 | 1.04 | Solid broken |
| 5 | 1.25 | 8.75 | 2 | 0.8626 | 0.52 | 0.03 | 0.52 | Thick light |
| 6 | 0.6 | 9.4 | 2 | 1.0217 | 0.25 | 0.03 | 0.25 | Normal viscosity lighter |
| 7 | 0.25 | 9.75 | 2 | 1.0020 | 0.10 | 0.03 | 0.10 | Normal viscosity lighter |

Modified-lignin wax emulsion sample 5 (Table 2) formed a thick coffee brown solution when intermixed into the commercial slack wax emulsion and produced a non-liquid formulation with limited suitability for wood composites applications.

Modified-lignin wax emulsion samples 6 and 7 (Table 2) formed liquid light brown solutions when intermixed into the commercial slack wax emulsion, that were stable for several days at room temperature. These modified-lignin wax emulsions were suitable for wood composites applications. These modified-lignin wax emulsions contained about 10-25% wt. of the novel lignin derivatives.

Example 2: Preparation of Lignin Wax Emulsions with Varying NaOH & LS Contents Modified-lignin wax emulsion samples were produced according to the recipes shown in Tables 3-6, with the following process steps:
(a) a solution comprising LS, NaOH and water was prepared following steps (a)-(b) from Example 1;
(b) a mixture of lignin derivatives was added to the solution at a ratio of about 1 g:2 g yielding about 33% lignin (by wt) in the solution;
(c) the lignin solution was exposed to ultrasound treatments and mixed thoroughly to produce a black paste;
(d) the black paste was combined with EW-58S wax emulsion at a ratio of 3:2, mixed thoroughly, and left to stand for two days at an ambient temperature.

TABLE 3

Preparation of the LS-NaOH solutions to produce lignin-modified slack wax emulsions with a final LS concentration of 0.3%

| Sample ID# | 7.4% NaOH added (mL) | Water (mL) | LS (mL) | [Final LS] (%) | [Final NaOH] (%) |
| --- | --- | --- | --- | --- | --- |
| 1A | 2.0 | 8.0 | 2.0 | 0.8 | 1.23 |
| 1B | 1.5 | 8.5 | 2.0 | 0.8 | 0.93 |
| 1C | 1.0 | 9.0 | 2.0 | 0.8 | 0.62 |

TABLE 3-continued

Preparation of the LS-NaOH solutions to produce lignin-modified slack wax emulsions with a final LS concentration of 0.3%

| Sample ID# | 7.4% NaOH added (mL) | Water (mL) | LS (mL) | [Final LS] (%) | [Final NaOH] (%) |
|---|---|---|---|---|---|
| 1D | 0.8 | 9.2 | 2.0 | 0.8 | 0.49 |
| 1E | 0.6 | 9.4 | 2.0 | 0.8 | 0.37 |
| 1F | 0.4 | 9.6 | 2.0 | 0.8 | 0.25 |

TABLE 4

Preparation of lignin-modified wax emulsions with a final LS concentration of 0.3%

| Sample ID# | LS-NaOH solution (g) | Lignin derivatives (g) | Wax emulsion (0.9 g/mL) | [Final LS] (%) | [Final NaOH] (%) | [Final lignin] (%) | [Final wax] (%) |
|---|---|---|---|---|---|---|---|
| 1A2 | 2.0 | 1.11 | 1.8 | 0.3 | 0.50 | 22.6 | 21.3 |
| 1B2 | 2.0 | 1.08 | 1.8 | 0.3 | 0.38 | 22.1 | 21.4 |
| 1C2 | 2.0 | 1.04 | 1.8 | 0.3 | 0.25 | 21.5 | 21.6 |
| 1D2 | 2.0 | 1.05 | 1.8 | 0.3 | 0.20 | 21.6 | 21.5 |
| 1E2 | 2.0 | 1.14 | 1.8 | 0.3 | 0.15 | 23.1 | 21.1 |
| 1F2 | 2.0 | 0.97 | 1.8 | 0.3 | 0.10 | 20.3 | 21.9 |

TABLE 5

Preparation of the LS-NaOH solutions to produce lignin-modified slack wax emulsions with a final LS concentration of 1.6%

| Sample ID# | 7.4% NaOH added (mL) | Water (mL) | LS (mL) | [Final LS] (%) | [Final NaOH] (%) |
|---|---|---|---|---|---|
| 2A | 2.0 | 8.0 | 2.0 | 2.3 | 1.23 |
| 2B | 1.5 | 8.5 | 2.0 | 3.9 | 0.93 |
| 2C | 1.0 | 9.0 | 2.0 | 3.9 | 0.62 |
| 2D | 0.8 | 9.2 | 2.0 | 3.9 | 0.49 |
| 2E | 0.6 | 9.4 | 2.0 | 3.9 | 0.37 |
| 2F | 0.4 | 9.6 | 2.0 | 3.9 | 0.25 |

TABLE 6

Preparation of lignin-modified wax emulsions with a final LS concentration of 1.6%

| Sample ID# | LS-NaOH solution (g) | Lignin derivatives (g) | Wax emulsion (0.9 g/mL) | [Final LS] (%) | [Final NaOH] (%) | [Final lignin] (%) | [Final wax] (%) |
|---|---|---|---|---|---|---|---|
| 2A2 | 2.0 | 1.03 | 1.8 | 1.0 | 0.51 | 21.3 | 21.6 |
| 2B2 | 2.0 | 0.94 | 1.8 | 1.6 | 0.39 | 19.8 | 22.0 |
| 2C2 | 2.0 | 1.01 | 1.8 | 1.6 | 0.26 | 21.0 | 21.7 |
| 2D2 | 2.0 | 1.14 | 1.8 | 1.6 | 0.20 | 23.1 | 21.1 |
| 2E2 | 2.0 | 1.02 | 1.8 | 1.6 | 0.15 | 21.2 | 21.7 |
| 2F2 | 2.0 | 1.05 | 1.8 | 1.6 | 0.10 | 21.6 | 21.5 |

Lignin-modified wax emulsion sample ID#s 1A2-1B2 resulted in black broken emulsions. Lignin-modified wax emulsion sample ID#s 1F2 resulted in a chocolate brown liquid with phase separation. Lignin-modified wax emulsion sample ID#s 1C2-1E2 conditions yielded liquid, chocolate brown formulations with evenly distributed precipitates. Lignin-modified wax emulsions sample ID #1C2 appeared to be the most homogenous formulation.

Lignin-modified wax emulsion sample ID#s 2A2-2B2 resulted in solid brown/black solid mass, broken emulsion. Lignin-modified wax emulsion sample ID #2C2 resulted in a slightly thick chocolate brown solution with precipitates, and showed some phase separation. Lignin-modified wax emulsion sample ID#s 2D2-2F2 resulted in a chocolate brown formulation containing some evenly distributed precipitates and particulate matter. Lignin-modified wax emulsion sample ID #1C2 yielded the best result formulation comprising a stable and uniform emulsion at 0.3% LS. The best formulation with a 1.6% LS final concentration was the lignin-modified wax emulsion sample ID #2C2 which had a slightly thicker composition in comparison to the series of wax emulsions produced with a 0.3% LS final concentration.

The optimal range of final NaOH concentrations was found to be about 0.25% to about 0.15% for the 0.3% LS series, and the optimal range of final NaOH concentrations in the 1.6% LS series was about 0.26% to about 0.10%.

The addition of excess NaOH appeared to break-down the lignin-modified wax emulsion into separated phases, although the lignin derivatives remained in solution. Lower final NaOH concentrations did not yield stable lignin-modified slack wax formulations in view of the particle aggregation that was observed in those compositions. The addition of the LS facilitated stable lignin-modified slack wax formulations. However, combinations of higher concentrations of both LS and NaOH resulted in thicker wax emulsions that are not particularly suitable for the manufacture of wood composite materials.

In this example, the concentrations of LS incorporated into the compositions were relatively higher compared to those used in Example #1, but were kept constant among a given dilution series (Tables 3 and 5). The final concentration achieved of LS was 0.3% for the first dilution series (Table 4) and 1.6% for the second dilution series (Table 6). Both dilution series were otherwise identical. The final NaOH concentration in the emulsions ranged from 0.1% to 0.5%. The concentration of lignin derivative mixtures was about 22% of the total final formulations. The final concentration of solids in the lignin-modified wax emulsions produced in this example was around 45% with the lignin derivatives comprising about half of the emulsions and the remainder comprising the commercial slack wax.

The increase in the lignin derivatives content produced stable wax emulsions suitable for use in production of OSB materials.

Example 3: Preparation of Lignin-Modified Wax Emulsions with Varying LS and Lignin Derivatives Contents Fifty-mL samples of modified-lignin wax emulsion samples were produced according to the recipes shown in Tables 7-10, following process steps outlined in Example 2. A first series was prepared wherein the final solids content in the modified-lignin wax emulsions was 54% solids, with approximately half comprising novel lignin derivatives solubilized and recovered from a hardwood lignocellulosic feedstock.

A second series was prepared wherein the final solids content in the modified-lignin wax emulsions was 56%, with 25% of that comprising the novel lignin derivatives.

TABLE 7

Preparation of the LS-NaOH solutions to produce lignin-modified slack wax emulsions with a final LS concentration of 1.0%, and comprising about 50% lignins.

| ID# | 7.4% NaOH added (mL) | Water (mL) | LS (mL) | [Final LS] (%) | [Final NaOH] (%) |
|---|---|---|---|---|---|
| 1C | 1.0 | 9.0 | 2.0 | 3.9 | 0.62 |
| 2C | 1.0 | 9.0 | 2.0 | 3.9 | 0.62 |
| 2D | 0.8 | 9.2 | 2.0 | 3.9 | 0.49 |
| 2E | 0.6 | 9.4 | 2.0 | 3.9 | 0.37 |

TABLE 8

Preparation of lignin-modified wax emulsions with a final LS concentration of about 1%

| ID# | LS-NaOH solution (g) | Lignin derivatives (g) | Wax emulsion (0.9 g/mL) | [Final LS] (%) | [Final NaOH] (%) | [Final lignin] (%) | [Final wax] (%) |
|---|---|---|---|---|---|---|---|
| 1C3 | 12.00 | 12.31 | 26.11 | 0.9 | 0.20 | 24.4 | 30.0 |
| 2C3 | 12.64 | 12.53 | 24.52 | 1.0 | 0.16 | 25.2 | 28.6 |
| 2D3 | 12.18 | 11.93 | 25.16 | 1.0 | 0.12 | 24.2 | 29.6 |
| 2E3 | 12.19 | 11.76 | 24.44 | 1.0 | 0.09 | 24.3 | 29.3 |

TABLE 9

Preparation of the LS-NaOH solutions to produce lignin-modified slack wax emulsions with a final LS concentration of 1.0%, and comprising about 25% lignins.

| ID# | LS-NaOH solution (g) | Lignin derivatives (g) | Wax emulsion (0.9 g/mL) | [Final LS] (%) | [Final NaOH] (%) | [Final lignin] (%) | [Final wax] (%) |
|---|---|---|---|---|---|---|---|
| 1C5 | 6.01 | 6.11 | 36.97 | 0.5 | 0.15 | 12.4 | 43.7 |
| 2C5 | 6.12 | 6.12 | 36.79 | 0.5 | 0.12 | 12.5 | 43.5 |
| 2D5 | 6.03 | 5.91 | 37.45 | 0.5 | 0.12 | 12.0 | 44.0 |
| 2E5 | 6.01 | 6.11 | 36.97 | 0.5 | 0.12 | 12.4 | 43.7 |

TABLE 10

Preparation of lignin-modified wax emulsions with a final LS concentration of 1.0%, and comprising about 25% lignins.

| | LS (g) (1 mL/g) | LS-NaOH soln (g) | Lignin deri. (g) | Wax emulsion (0.9 g/mL) | [Final LS] (%) | [Final NaOH] (%) | [Final lignin] (%) | [Final wax] (%) |
|---|---|---|---|---|---|---|---|---|
| 2D11 | 117.27 | 0 | 116.34 | 240.0 | 1.0 | 0.12 | 24.6 | 29.4 |

| ID# | Final Mass (g) | Total solids (%) | % lignin of total solids | % lignin of total solids |
|---|---|---|---|---|
| 2D11 | 6.01 | 6.11 | 36.97 | 0.5 |

All of the samples produced with the recipes shown in Tables 7-10 comprised liquid lignin-modified slack wax emulsions. Lignin-modified wax emulsion sample ID#s 1C3-2E3 (~50:50 lignin/wax) were liquid and were about the same chocolate brown color. All samples had visually detectable particles distributed throughout emulsions. Lignin-modified wax emulsion sample ID#s 1C5-2E5 (~25/75 lignin/wax) were almost identical in color. These samples were of a grey/brown color that was significantly lighter than the color of lignin-modified wax emulsion sample ID#s 1C3-2E3.

The preceding examples exemplify methods of the present invention for preparing lignin-modified wax emulsions comprising lignin derivatives solubilized during and recovered from organosolv pulping of lignocellulosic biomass sources.

Example 4: OSB Panels Prepared with a Lignin-Modified Wax Emulsion

Lignin-modified wax emulsion sample ID#s 2D5 and 2D11 were prepared in 250-mL volumes following the process steps outlined in Example 3, and were used for production of OSB panels. Three types of homogenous OSB panels were produced in triplicate using aspen strands as the feedstock. The strands were screened to remove fines and then dried to about 2% moisture content prior to blending with a commercial liquid OSB face phenol-formaldehyde resin (EW-58S emulsion). The EW-58S emulsion was added at 3% (dry wood basis). The target moisture content of strands after blending was 5.5%. The commingled aspen strand—EW-58S emulsion was passed through a conventional press set at a target density of 40 lb/ft³ to produce panels having a thickness of 0.4375 inches.

The first set of three OSB panels were the controls produced with the EW-58S emulsion with the following process steps:
(a) aspen strands were screened to remove fines;
(b) 14 kg aspen strands were dried to about 2% moisture content (MC);
(c) the liquid PF resin OSF-59LFM was warmed to 25° C.;
(d) the blending was conducted using the following parameters:
strands: 14 kg dry Aspen/blend (2% MC)
wax emulsion: 241 g EW-58S
phenol-formaldehyde resin: (59% solids): 711 g of OSF-59FLM resin
(e) resinated furnish was checked for moisture content.
(f) each mat was formed manually with care to ensure even density distribution across the face of each panel.
(g) each panel was pressed with the following parameters:
weight of dispensed materials: 3665 g/mat
dimensions: 28"×28"×7/16"
density: 40 lb/f³
press temperature: 210° C.
press time: 4 minutes
(h) the control OSB panels were labeled C1-C3

The second set of three OSB panels were produced following the same process steps listed for the control OSB panels except that the wax emulsion in step (d) was substituted with lignin-modified wax emulsion sample ID #2D11 (50%:50% lignol:wax ratio). The three OSB panels produced with lignin-modified wax emulsion sample ID #2D5, were labeled E5-E7.

The third set of three OSB panels were produced following the same process steps listed for the control OSB panels except that the wax emulsion in step (d) was substituted with lignin-modified wax emulsion sample ID #2D5 (25%:75% lignol:wax ratio). The three OSB panels produced with lignin-modified wax emulsion sample ID #2D5, were labeled E1-E3.

Each of the three panels from each blend was tested for: (a) density, (b) internal bond strength (IB), (c) bond durability using MOR and MOE determinations (MOR=modulus of rupture; MOE=modulus of elasticity), (d) thickness swell and water absorption after (i) a 24-hour submerged water soaking, and (ii) a 2-hour period of boiling in water. The above tests were conducted following the Canadian Standard #0437.1-93 Test Methods for OSB and Waferboard (ISSN 0317-5669, published in April 1993 by Canadian Standards Association, Toronto, ON, Canada). The testing results are shown in Tables 11-13.

TABLE 11

| Panel ID # | Panel density (lb/ft³) | IB density (lb/ft³) | Internal bond strength (MPa) | TSWA* density (lb/ft³) |
| --- | --- | --- | --- | --- |
| C1 | 41.0 | 42.6 | 0.256 | 43.5 |
| C2 | 40.0 | 38.8 | 0.216 | 41.8 |
| C3 | 39.9 | 40.6 | 0.238 | 40.0 |
| C1-C2 mean | 40.3 | 40.7 | 0.237 | 41.8 |
| E1 | 40.3 | 39.7 | 0.212 | 42.0 |
| E2 | 39.6 | 38.9 | 0.206 | 41.4 |
| E3 | 40.2 | 40.5 | 0.266 | 42.2 |
| E1-E3 mean | 40.0 | 39.7 | 0.228 | 41.9 |
| E5 | 39.5 | 39.2 | 0.139 | 41.4 |
| E6 | 39.6 | 37.1 | 0.155 | 40.1 |
| E7 | 39.5 | 39.9 | 0.132 | 42.7 |
| E5-E7 mean | 39.5 | 38.7 | 0.142 | 41.4 |

*TSWA is "Thickness swell and water absorption".

TABLE 12

| Panel ID # | % thickness swelling (24-h soak) | % water absorption (24-h soak) | % thickness swelling (24-h soak + 2-h boil) | % water absorption (24-h soak + 2-h boil) |
| --- | --- | --- | --- | --- |
| C1 | 20.3 | 30.3 | 75.3 | 142.3 |
| C2 | 20.2 | 31.5 | 66.4 | 141.6 |
| C3 | 19.8 | 31.6 | 64.1 | 142.9 |
| C1-C2 mean | 20.1 | 31.1 | 68.6 | 142.3 |
| E1 | 20.0 | 31.5 | 65.0 | 141.8 |
| E2 | 22.9 | 34.1 | 72.0 | 141.6 |
| E3 | 23.7 | 34.3 | 67.7 | 140.6 |
| E1-E3 mean | 22.2 | 33.3 | 68.2 | 143.1 |
| E5 | 26.7 | 41.5 | 78.3 | 150.4 |
| E6 | 30.0 | 44.7 | 79.2 | 155.8 |
| E7 | 29.5 | 41.1 | 87.4 | 153.2 |
| E5-E7 mean | 28.7 | 42.4 | 81.6 | 153.1 |

TABLE 13

| Panel ID # | Dry bending density (lb ft³) | Dry MOR (MPa) | Dry MOE (MPa) | Wet bending density (lb ft³) | Wet bending MOR (MPa) |
| --- | --- | --- | --- | --- | --- |
| C1 | 40.9 | 30.40 | 4596 | 41.3 | 11.99 |
| C2 | 41.4 | 25.75 | 3824 | 39.9 | 9.25 |
| C3 | 42.0 | 32.22 | 4510 | 38.5 | 9.25 |
| C1-C2 mean | 41.4 | 29.46 | 4310 | 39.9 | 10.16 |
| E1 | 42.6 | 31.72 | 4971 | 40.8 | 11.60 |
| E2 | 40.7 | 26.16 | 3670 | 40.4 | 11.56 |
| E3 | 40.9 | 33.22 | 4061 | 40.2 | 11.00 |
| E1-E3 mean | 41.4 | 30.37 | 4234 | 40.5 | 11.39 |
| E5 | 39.7 | 22.86 | 3823 | 39.4 | 4.99 |
| E6 | 41.7 | 26.51 | 3984 | 40.4 | 6.81 |

TABLE 13-continued

| Panel ID # | Dry bending density (lb ft³) | Dry MOR (MPa) | Dry MOE (MPa) | Wet bending density (lb ft³) | Wet bending MOR (MPa) |
|---|---|---|---|---|---|
| E7 | 40.0 | 22.16 | 3580 | 39.5 | 6.37 |
| E5-E7 mean | 40.5 | 23.84 | 3796 | 39.8 | 6.06 |

OSB panels prepared with lignin-modified wax emulsion sample ID #2D5 (i.e., panels E1-E3) performed similarly to OSB panels prepared with the commercial slack wax EW-58S (i.e., panels C1-C3). Lignin-modified wax emulsion sample ID #2D5 comprised a 25%:75% lignol:wax ratio. These data indicate that 25% of a commercial slack wax emulsion used for production of OSB materials, can be replaced with lignin derivatives.

The invention claimed is:

1. A composite wood product comprising a wax emulsion comprising:
   a lignin derivative extracted from a lignocellulosic biomass, wherein the lignin derivative comprises a total hydroxyl content of from about 0.1 mmol/g to about 7 mmol/g; and
   a wax;
   wherein the wax emulsion comprises, on a solid content basis, about 10% or greater by weight of the lignin derivative.

2. The composite wood product according to claim 1, wherein the total hydroxyl content is from about 3 mmol/g to about 6.4 mmol/g.

3. The composite wood product according to claim 1, wherein the lignin derivative further comprising alkoxy groups.

4. The composite wood product according to claim 1, wherein the lignocellulosic biomass is from a hardwood biomass, a softwood biomass, or an annual fibre biomass.

5. The composite wood product according to claim 1, wherein the lignocellulosic biomass is from *Populus* spp., *Eucalyptus* spp., *Acacia* spp., or any combination/hybrid thereof.

6. The composite wood product according to claim 1, wherein the lignocellulosic biomass is from pine, spruce, or any combination/hybrid thereof.

7. The composite wood product according to claim 1, wherein the lignocellulosic biomass is from wheat straw, bagasse, corn cobs, or any combination/hybrid thereof.

8. The composite wood product according to claim 1, wherein the wax is a slack wax.

9. The composite wood product according to claim 1, wherein the wax emulsion comprises, on a solid content basis, from about 20% to about 90%, by weight of the lignin derivative.

10. The composite wood product according to claim 1, comprising, on a solid content basis, from about 1% to about 90%, by weight of the wax.

11. The composite wood product according to claim 8, comprising, on a solid content basis, from about 20% to about 90%, by weight of the slack wax.

12. The composite wood product according to claim 1, the lignin derivative having a weight average molecular weight from about 500 g/mol to about 5000 g/mol.

13. The composite wood product according to claim 1, further comprising a surface tension reducing agent or an interfacial tension reducing agent, and a lignin solubilizing agent.

14. The composite wood product according to claim 13, wherein the surface tension reducing agent or the interfacial tension reducing agent is a lignosulphate, an isogenic lignin derivative, an ionogenic detergent or a combination thereof.

15. The composite wood product according to claim 14, wherein the ionogenic detergent is sodium dodecyl sulfate.

16. A method of producing the composite wood product according to claim 1, the method comprising:
   (a) preparing an aqueous solution comprising one of a surface tension reducing agent and an interfacial tension reducing agent;
   (b) co-mingling with the aqueous solution a selected amount of a base, thereby forming a basic aqueous solution;
   (c) co-mingling with the basic aqueous solution a selected amount of a lignin derivative having a total hydroxyl content of from about 0.1 mmol/g to about 7 mmol/g, thereby forming a mixture;
   (d) separating the mixture into a filtrate and a retentate, wherein the lignin derivative is co-mingled with the filtrate;
   (e) co-mingling a selected volume of the filtrate with a selected volume of a wax to form a wax emulsion; and
   (f) blending and pressing the wax emulsion with a wood feedstock and a phenol-formaldehyde resin to form the composite wood product.

17. The method according to claim 16, wherein the one of a surface tension reducing agent and an interfacial tension reducing agent is selected from the group consisting of lingo-sulphonates, isogenic lignin derivatives, ionogenic detergents, and any combination thereof.

* * * * *